(12) United States Patent
Lauks et al.

(10) Patent No.: US 7,767,068 B2
(45) Date of Patent: Aug. 3, 2010

(54) HETEROGENEOUS MEMBRANE ELECTRODES

(75) Inventors: Imants Lauks, Ottawa (CA); Anca Varlan, Nepean (CA); Alexandra Oussova, Ottawa (CA); Michael Bales, Ottawa (CA)

(73) Assignee: Epocal Inc., Ottawa (CA)

( * ) Notice: Subject to any disclaimer, the term of this patent is extended or adjusted under 35 U.S.C. 154(b) by 1174 days.

(21) Appl. No.: 10/856,929

(22) Filed: Jun. 1, 2004

(65) Prior Publication Data

US 2004/0231984 A1    Nov. 25, 2004

Related U.S. Application Data

(63) Continuation-in-part of application No. 10/307,481, filed on Dec. 2, 2002, now Pat. No. 7,094,330.

(51) Int. Cl.
*G01N 27/26* (2006.01)
(52) U.S. Cl. ........................ 204/416; 204/431
(58) Field of Classification Search ........... 204/416, 204/431
See application file for complete search history.

(56) References Cited

U.S. PATENT DOCUMENTS

| | | | |
|---|---|---|---|
| 4,062,750 A | 12/1977 | Butler | |
| 4,133,735 A | 1/1979 | Afromowitz et al. | |
| 4,225,410 A | 9/1980 | Pace | |
| 4,276,141 A | 6/1981 | Hawkins | |
| 4,301,412 A | 11/1981 | Hill et al. | |
| 4,342,964 A | 8/1982 | Diamond et al. | |
| 4,431,508 A * | 2/1984 | Brown et al. ......... | 204/418 |
| 4,436,610 A | 3/1984 | Enzer et al. | |
| 4,534,356 A | 8/1985 | Papadakis | |
| 4,551,209 A | 11/1985 | Lauks | |
| 4,592,824 A | 6/1986 | Smith et al. | |
| 4,613,422 A | 9/1986 | Lauks | |
| 4,629,424 A | 12/1986 | Lauks et al. | |

(Continued)

FOREIGN PATENT DOCUMENTS

EP    0 325 562    7/1989

(Continued)

OTHER PUBLICATIONS

Matysik et al, "A Disposable Electrode Based on Zeolite-Polymer Membranes for Potentiometric Titrations of Ionic Surfactants", *Sens Actuators, B. Chem; Sensors and Actuators, B: Chemical*, Jun. 20, 2002, vol. 85, No. 1-2, pp. 104-108, XP002271483.

(Continued)

*Primary Examiner*—Jennifer K Michener
*Assistant Examiner*—Dustin Q Dam
(74) *Attorney, Agent, or Firm*—Borden Ladner Gervais LLP

(57) ABSTRACT

The present invention relates to planar electrochemical sensors with membrane coatings used to perform chemical analyses. The object of this invention is to provide unit-use disposable sensors of very simple and inexpensive construction, preferably with only a single membrane coating on an electrode. The invented devices are potentiometric salt-bridge reference electrodes and dissolved gas sensors constructed with a heterogeneous membrane coating of a conductor. The heterogeneous membrane, which is an intimate admixture of a hydrophobic and a hydrophilic compartment, concurrently supports constrained transport of non-volatile species through its hydrophilic compartment and rapid gas and water vapor transport through its hydrophobic compartment.

38 Claims, 6 Drawing Sheets

U.S. PATENT DOCUMENTS

| | | | |
|---|---|---|---|
| 4,654,127 A | 3/1987 | Baker et al. | |
| 4,682,602 A | 7/1987 | Prohaska | |
| 4,689,309 A | 8/1987 | Jones | |
| 4,734,184 A | 3/1988 | Burleigh et al. | |
| 4,739,380 A | 4/1988 | Lauks et al. | |
| 4,864,229 A | 9/1989 | Lauks et al. | |
| 4,877,528 A * | 10/1989 | Friesen et al. | 210/500.29 |
| 4,933,048 A | 6/1990 | Lauks | |
| 4,954,087 A | 9/1990 | Lauks et al. | |
| 5,008,616 A | 4/1991 | Lauks et al. | |
| 5,009,766 A | 4/1991 | Lauks | |
| 5,030,310 A | 7/1991 | Wogoman | |
| 5,063,081 A | 11/1991 | Cozzette et al. | |
| 5,078,854 A | 1/1992 | Burgess et al. | |
| 5,096,669 A | 3/1992 | Lauks et al. | |
| 5,112,455 A | 5/1992 | Cozzette et al. | |
| 5,124,661 A | 6/1992 | Zelin et al. | |
| 5,141,868 A | 8/1992 | Shanks et al. | |
| D332,833 S | 1/1993 | Lauks et al. | |
| 5,183,549 A | 2/1993 | Joseph et al. | |
| 5,200,051 A | 4/1993 | Cozzette et al. | |
| 5,212,050 A | 5/1993 | Mier et al. | |
| D337,164 S | 7/1993 | Lauks et al. | |
| 5,246,576 A | 9/1993 | Leader et al. | |
| 5,325,853 A | 7/1994 | Morris et al. | |
| 5,385,659 A | 1/1995 | Gumbrecht et al. | |
| 5,416,026 A | 5/1995 | Davis | |
| 5,445,920 A | 8/1995 | Saito | |
| 5,447,440 A | 9/1995 | Davis et al. | |
| 5,466,575 A | 11/1995 | Cozzette et al. | |
| 5,496,521 A | 3/1996 | Leiner | |
| 5,514,253 A | 5/1996 | Davis et al. | |
| 5,554,272 A | 9/1996 | Benco et al. | |
| 5,554,339 A | 9/1996 | Cozzette et al. | |
| 5,593,638 A | 1/1997 | Davis | |
| 5,605,664 A | 2/1997 | Lauks et al. | |
| 5,609,824 A | 3/1997 | Lauks et al. | |
| 5,614,416 A | 3/1997 | Lauks et al. | |
| 5,628,961 A | 5/1997 | Davis et al. | |
| 5,638,828 A | 6/1997 | Lauks et al. | |
| 5,653,243 A | 8/1997 | Lauks et al. | |
| 5,658,444 A | 8/1997 | Black et al. | |
| 5,666,967 A | 9/1997 | Lauks et al. | |
| 5,708,247 A | 1/1998 | McAleer et al. | |
| 5,727,548 A | 3/1998 | Hill et al. | |
| 5,779,650 A | 7/1998 | Lauks et al. | |
| 5,789,253 A | 8/1998 | Lauks et al. | |
| 5,821,399 A | 10/1998 | Zelin | |
| 5,837,446 A | 11/1998 | Cozzette et al. | |
| 5,837,454 A | 11/1998 | Cozzette et al. | |
| 5,900,215 A * | 5/1999 | Seifert et al. | 422/82.07 |
| 6,010,463 A | 1/2000 | Lauks et al. | |
| 6,030,827 A | 2/2000 | Davis et al. | |
| 6,306,594 B1 | 10/2001 | Cozzette et al. | |
| 6,379,883 B2 | 4/2002 | Davis et al. | |
| 6,432,296 B1 | 8/2002 | Daniel et al. | |
| 6,438,498 B1 | 8/2002 | Opalsky et al. | |
| 6,484,045 B1 * | 11/2002 | Holker et al. | 600/345 |
| 6,750,053 B1 | 6/2004 | Opalsky et al. | |
| 6,766,817 B2 | 7/2004 | da Silva | |
| 7,074,610 B2 | 7/2006 | Cozzette et al. | |
| 7,087,149 B1 * | 8/2006 | Muguruma et al. | 205/778 |
| 2002/0011408 A1 * | 1/2002 | Lee et al. | 204/414 |
| 2002/0177958 A1 | 11/2002 | Opalsky et al. | |
| 2002/0179444 A1 | 12/2002 | Lauks | |
| 2003/0148530 A1 | 8/2003 | Lauks | |
| 2003/0170881 A1 | 9/2003 | Davis et al. | |
| 2004/0018577 A1 | 1/2004 | Campbell et al. | |
| 2004/0175296 A1 | 9/2004 | Opalsky et al. | |
| 2005/0054078 A1 | 3/2005 | Miller et al. | |
| 2006/0046275 A1 | 3/2006 | Collier et al. | |
| 2006/0160164 A1 | 7/2006 | Miller et al. | |
| 2007/0015977 A1 | 1/2007 | McCann et al. | |

FOREIGN PATENT DOCUMENTS

| | | |
|---|---|---|
| EP | 0 551 769 | 7/1993 |
| EP | 1 087 225 | 3/2001 |
| EP | 1 193 495 | 4/2002 |
| EP | 1193495 A2 * | 4/2002 |
| GB | 1 584 788 | 2/1981 |
| JP | 2087067 | 3/1990 |
| JP | 9299445 | 11/1997 |
| JP | 11083783 A | 3/1999 |
| RO | 81891 * | 5/1983 |
| RO | 81891 A | 5/1983 |
| WO | WO 00/58720 | 10/2000 |
| WO | WO 0063685 * | 10/2000 |
| WO | 03/034056 A1 | 4/2003 |

OTHER PUBLICATIONS

Sinsabaugh et al., "A Batch-Processed Reference Micro Electrode Integratred on a Silicon Substrate", *Department of Electrical Engineering & Applied Physics and Electronics Design Center*, vol. 86, issue 14, 1986, pp. 66-73.

Janata et al., "Solid State Chemical Sensors", 1985, pp. 101-103.

Japanese Patent Application No. 2004-555906, Office Action dated Dec. 1, 2009.

Japanese Patent Application No. 513633/2007: Office Action dated May 19, 2009.

Japanese Patent Application No. 513633/2007, Office Action dated Nov. 17, 2009 (English Translation).

* cited by examiner

HETEROGENEOUS MEMBRANE ELECTRODES

CROSS REFERENCE TO RELATED APPLICATIONS

This application is a continuation in part to U.S. patent application Ser. No. 10/307,481 filed Dec. 2, 2002 now U.S. Pat. No. 7,094,330, and entitled "Heterogeneous Membrane Electrodes", which is incorporated into the present application in its entirety.

FIELD OF INVENTION

The invention relates to diagnostic devices comprising electrochemical sensors for the analysis of aqueous solutions including clinical samples. In particular, the invention relates to the construction of unit-use indicator and reference electrodes for such devices.

BACKGROUND OF THE INVENTION

Prior-art electrochemical sensors typically consist of an electrochemical cell with two, sometimes three electrodes. The first electrode is responsive to a chemical species in the test solution and is called the indicator electrode. The second electrode called the reference electrode is typically non-responsive to changes in the composition of the test solution. In polarography a third, current-injecting counter electrode is sometimes used.

As is appreciated by those in the art, the performance of an electrochemical sensor as part of a chemistry analyzer for quantitative measurement of chemicals in aqueous solutions is determined by its dose-response curve. For a linear sensor this can be uniquely determined by two coefficients: a slope and an intercept. For a dose-response curve that is non-linear, three or more coefficients may be required. As is also known in the art, a sensor's coefficients vary over time if it is used more than once. The coefficients also vary from sensor to sensor because no two sensors can be manufactured identically. Therefore, a calibration is generally required to uniquely determine a sensor's dose-response curve. In an automated chemistry analyzer the calibration is provided by fluidic elements (calibration fluids, pumps, valves, conduits etc.) contained within the analyzer. If a sensor is deployed as a reusable device it is often the case that the chemistry analyzer's calibration fluidics provides for at least two calibration points and a wash solution. This is because slope and intercept of the dose-response curve can change through repeated uses. For a unit-use device no calibration would be required if the slope and intercept were sufficiently reproducible from sensor to sensor during manufacture and storage. A single calibrator would be required if either one of the coefficients was reproducible, the other not, and two calibrators if neither coefficient was reproducible (more calibrators could be required for devices with non-linear dose-response curves).

Often the goal of a manufacturer of chemistry analyzers is to produce sensors sufficiently cheaply so that they can be deployed as unit-use devices, thus eliminating or simplifying the chemistry analyzer's often very complex fluidics required for the washing and calibrating of multiple-use sensors. To this end, manufacturers have investigated planar technologies for low cost sensor manufacture. Such technologies also purport to provide appropriate control of the materials of construction and manufacturing processes to achieve device-to-device reproducibility in high volume production.

Sensors made by planar technology have included both thick-film and thin-film micro-fabrication technologies. Thick film processed devices such as plastic diagnostic strips are disclosed in U.S. Pat. No. 5,727,548 for example. Devices made by planar technology also include thick film processed planar substrates as in hybrid circuit or printed circuit manufacture. U.S. Pat. Nos. 4,133,735, 4,225,410 for example disclose devices with electrodes made by thick film fabrication processes such as plating, screen-printing, dispensing and the like.

Micro-fabrication technology with its proven superior dimensional control also has been used to make devices for unit-use applications. Micro-fabrication technology employs wafer-level processes such as photolithography on silicon wafers. U.S. Pat. Nos. 4,062,750 4,933,048 and 5,063,081 disclose devices containing electrodes made by thin-film micro-fabrication processes on silicon substrates.

Regardless of which of the above variants of planar technology is being used, planar devices of the prior art have been complex to manufacture and are therefore still expensive.

To better appreciate the complexity of prior-art planar sensors, consider their typical components of construction. A planar electrochemical sensor of the prior art is a device consisting of one or more metal conductor elements on a planar insulating substrate. One region of the metal conductor element is provided for connection to an external measuring circuit. A planar electrode is formed in another region of the metal conductor element. The planar electrode of such a prior-art electrochemical sensor consists typically of one or more additional metal layers (or other electrical conductors such as graphite) and insoluble metal salt over-layers overcoating the metal conductor element. Planar electrodes are typically then coated with several additional functional layers as outlined below.

The planar electrode of the planar sensor is typically coated by an integral electrolyte medium. This integral electrolyte may be a liquid aqueous solution or, more commonly, a solid hydrophilic layer such as a gel material that acts like an aqueous electrolyte. In use of the planar sensor, the planar electrode region and its integral electrolyte over-layer is immersed in an aqueous solution to be tested. Chemical species from the test solution permeate into the integral electrolyte layer, dissolve and often react with other reagents contained within the integral electrolyte layer. Components of the integral electrolyte layer undergo electrochemical reaction at the electrode surface generating a current or a voltage. When the measured current or voltage of the sensor is selectively proportional to the concentration of a species in the test solution that is transported from the test solution into the sensor there is the basis for an indicator electrode for that species. If the voltage is independent of test solution composition there is the basis for a reference electrode. In prior-art electrochemical sensors it is generally required that chemical reagents within the integral electrolyte layer be at constant concentrations during the time of the measurement.

It is generally required that chemicals contained within the test solution that are deleterious to the sensor reactions be rejected from the integral electrolyte layer. As is known in the art such contaminants may affect chemical reactions within the integral electrolyte layer, or they may themselves be electro-active and cause a voltage or current that interferes with the measured voltage or current due to the species being analyzed. Retention of reagent chemical and rejection of contaminants is achieved by interposing one or more materials between the integral electrolyte and the test solution. Transport of the sensed species from the test solution into the integral electrolyte layer takes place by selective diffusion through the interposed materials. In many cases of prior-art planar sensors it is also necessary to interpose an additional semi-permeable layer between the electrode and the integral electrolyte layer. The purpose of this electrode-modifying layer is to allow transport of the chemicals of the sensor reaction while rejecting electroactive interferents or species that poison the electrode.

In summary, as described above, planar electrochemical sensors of the prior art including the prior-art reference electrodes, enzyme electrodes and gas sensing electrodes generally consist of numerous elements. The resulting devices are complex and costly to manufacture. To further illustrate their complexity, the devices of the prior art in each of the above categories addressed by the current invention are described in more detail in the following sections.

Potentiometric Salt-Bridge Reference Electrode Prior Art

Salt-bridge reference electrodes of the prior art consists of an electrode, usually silver with a silver chloride over-layer which is contacted by an integral reservoir of a concentrated aqueous solution of a salt with equi-mobile ions, typically potassium chloride. The electrolyte reservoir contacts the test solution through a constrained-flow liquid junction, which is typically a micro-porous element. The integral aqueous electrolyte reservoir and the junction together comprise a salt bridge. An ideal salt-bridge reference electrode of this design has an essentially constant electrode potential and essentially zero response slope for the duration of its use. As is known in the art of reference electrodes, the total electrode potential is the sum of the potential difference between the electrode and integral salt-bridge electrolyte and the liquid-junction potential difference which is between the salt-bridge electrolyte and the test solution. The constant electrode potential of such prior-art reference electrodes is achieved firstly because the potential determining chloride concentration of the salt-bridge electrolyte at the silver-silver chloride electrode surface remains essentially fixed for the duration of use. This is achieved both because the rate of chloride efflux from the reservoir into the test solution is sufficiently small because of the constrained-flow junction and because the electrolyte reservoir is sufficiently large. Secondly, the response slope of such salt-bridge reference electrode is also small when the liquid junction potential difference is small as is the case when the salt-bridge electrolyte contains a concentrated salt with anions and cations of nearly equal mobility, such as with the use of a concentrated potassium chloride electrolyte.

Planar potentiometric salt-bridge reference electrodes of the prior art have used the same approach as the classical salt-bridge reference electrode described above. U.S. Pat. No. 4,592,824 describes a planar silver-silver chloride electrode on a planar silicon substrate, and a silicon cover-plate including a micro-fabricated cavity and porous region. The cavity including the porous junction becomes the integral salt-bridge reservoir when it is filled with concentrated potassium chloride before use. The porous silicon element forms the region of the constrained-flow liquid junction that contacts the test solution. Similarly, U.S. Pat. No. 4,682,602 describes a planar silver-silver chloride electrode and a cover layer defining a cavity over the electrode. The cavity, when filled with electrolyte, becomes the integral salt-bridge reservoir. There is a small aperture providing a flow-constraining liquid junction contact to a test solution. U.S. Pat. No. 5,385,659 describes a planar silver-silver chloride with a micro-fabricated, elongated cavity in a cover plate. When the elongated cavity is filled with electrolyte it becomes the integral salt bridge reservoir. The flow of electrolyte out of the salt-bridge is constrained because the cavity is elongated and its opening is small. These and other prior-art planar reference electrodes with integral electrolyte cavities are relatively complex and costly assemblies. They must be filled with concentrated salt-bridge electrolyte before use, or, if filled in the factory, they must be stored wet. Consequently, they are impractical for unit-use applications.

U.S. Pat. No. 4,342,964 describes a fluidic cassette for blood measurement containing a dry-stored silver-silver chloride electrode without an integral salt-bridge electrolyte over-layer and a spaced apart indicator electrode. In use, a calibrator solution is introduced over the pair of electrodes serving to calibrate the indicator electrode prior to its subsequent exposure to the test solution. The calibrator solution also fills an empty cavity region of the cassette over the silver-silver chloride electrode and remains there to form a liquid junction with the test solution when it is subsequently introduced into the cassette. Thus, this patent teaches how to automatically fill a reference electrode's salt-bridge reservoir without significantly adding to the complexity of the reference electrode itself, because the device already requires a calibrator solution and the patent teaches that the calibrator solution can be the same as the salt-bridge filling solution. However there is added fluidic complexity and cost, and the significant limitation on this invention is that there is no single composition of the calibrator solution that is satisfactory both to accurately calibrate the indicator electrode and provide for a low-response liquid junction. For acceptable performance in blood it is known in the art that the salt-bridge electrolyte should have a potassium chloride concentration of about 1M or even larger for the liquid junction potential component of the reference electrode to be acceptably small and constant. Known calibrator solutions for blood do not provide this concentration Janata in *Solid State Chemical Sensors*, Janata J. and Huber R. J. (eds.), Academic Press Inc., Orlando 1985, pp 101-103, describe an ion-sensitive field effect reference electrode with an integral salt-bridge reservoir formed by a hydrophilic gel layer coating the electrode. Sinsabaugh et al. in *Proceedings, Symposium on Electrochemical Sensors for Biomedical Applications*, Vol. 86-14, Conan, K. N. L. (ed.), The Electrochemical Society, Pennington, N.J. 1986, pp 66-73, describe a planar reference electrode consisting of a silver-silver chloride electrode over-coated by an integral salt-bridge reservoir formed by a latex membrane. In this device there are in total three coating steps onto the conductor element and its support. The Janata and Sinsabaugh devices were intended for multi-use sensor applications utilizing a calibrator solution. In a typical measurement the reference electrode, with its salt-bridge reservoir over-layer, and a spaced-apart indicator electrode are first immersed in a calibrator solution. The integral reservoir equilibrates to the concentration of the calibrator solution. When the electrode-pair is then immersed in a test solution the indicator electrode responds rapidly but, because of its integral constrained-flow reservoir, the potential difference between the silver-silver chloride and the salt-bridge electrolyte over-layer responds slowly. If the reservoir thickness is sufficient (several hundred micrometers) the response is slow enough to constitute a constant potential over the time that the indicator electrode responds (approximately 10 s). During multiple uses the composition of the salt-bridge gradually approaches the concentration of the calibrator and test solutions in which it is immersed. These reference electrodes in multi-use application are once again limited in utility for accurate blood measurements because the liquid junction component of the reference electrode potential is not sufficiently small or constant because the salt-bridge reservoir concentration is too low. Both these papers are silent on the use of their salt-bridge reservoirs as dry-reagent formulations in unit-use reference electrodes. Both papers are silent on the incorporation of redox chemicals into the salt-bridge reservoirs and the use of such in reference electrodes constructed with salt-bridges coating metals. The Sinsabaugh paper is also silent on the water vapor transport properties of their latex membrane formulation.

Because of the complexity of manufacture of reference electrodes containing integral fluid reservoirs and because of the difficulty of their storage and preparation for use, a dry-reagent reference electrode is highly desirable for unit-use applications. An integral dry-reagent salt-bridge reservoir that contains only dry salts must first acquire water so that the salt-bridge reservoir can 'wet up' to its operational concentration. In all of the above-mentioned prior-art devices the transport of species through the salt-bridge reservoir and from the salt bridge to the contacting solution is through an electrolyte phase. Water influx for wet-up of the prior-art devices dry reagent devices is through the same path as potassium chloride efflux. Thus, in a device featuring a constrained flow salt-bridge design with a sizeable reservoir that is required to maintain constancy of chloride concentration at the silver-silver chloride surface, the time for water uptake also will be large. Also, the potassium chloride of the salt bridge electrolyte will escape from the reservoir into the solution while the reservoir is acquiring water from the solution for its wet-up. Therefore, reference electrodes with dry reagent reservoirs according to the above prior art have not been successfully deployed in unit-use applications.

The above wet-up problem was addressed in U.S. Pat. No. 4,933,048, which describes a dry-reagent salt-bridge reference electrode made by planar micro-fabrication. In this device there is a first insulating layer on a planar substrate that supports a conductor for connection to a measuring circuit. A second insulating layer covers the conductor except in a region that defines the electrode opening. There are films of silver, then silver chloride formed over the conductor in the electrode region. A solid hydrophilic material containing potassium chloride is formed over the silver chloride. This layer constitutes the integral salt-bridge reservoir. In this device, the salt-bridge reservoir extends well beyond the silver-silver chloride electrode edge and is further coated by a hydrophobic water vapor-permeable over-layer, except for a region of the salt bridge that is far removed from the silver-silver chloride where the salt-bridge contacts the test fluid defining the liquid junction. This unit-use salt-bridge reference electrode was designed to rapidly wet-up during use from its dry storage state, and to essentially retain a constantly high concentration of potassium chloride in the integral salt-bridge reservoir for a period after full wet-up and through the time of the measurement. These desired properties are obtained in the device of the '048 patent by providing a short diffusion path for rapid water influx into the integral reservoir through the water vapor-permeable over-layer and a long diffusion path for the potassium chloride in the salt-bridge along the length of the integral reservoir. In use, the water necessary for the proper function of the salt bridge is rapidly incorporated into the initially dry potassium chloride layer within a few seconds by diffusion through the gas permeable over-layer. The concentration of the internal salt-bridge electrolyte rapidly reaches a steady state value after a wet-up period of a few seconds which is maintained for a period sufficient to perform the potentiometric measurement. However, this device is complex to manufacture, consisting of five layers on top of the conductor element and its insulating support.

U.S. Pat. No. 4,431,508 describes a graphite reference electrode with a hydrophilic coating containing a redox couple manufactured with non-planar conventional technology.

In summary, planar reference electrodes of the prior art consist of a silver-silver chloride electrode contacting an integral salt-bridge electrolyte reservoir consisting of concentrated potassium chloride. These devices are either manufactured with water already incorporated into the salt-bridge reservoir, or, they are dry-reagent devices with a gas permeable coating that facilitates water transport into the salt bridge. The salt bridge makes connection to the test solution through a small, flow-constraining orifice or other flow limiting physical constriction fabricated on the device in planar technology. The connection of the salt bridge to the test solution is at a point removed from the silver-silver chloride electrode, so that an integral reservoir of electrolyte is present between the solution and the electrode.

Potentiometric Dissolved Gas Sensor Prior Art

The carbon dioxide sensor is exemplary of potentiometric gas sensors of the prior-art. U.S. Pat. No. 4,734,184 is one typical example from a large literature of planar carbon dioxide sensors. In this example the device consists of a planar insulating substrate with two conductor elements for connection to a measuring circuit. Assembled thereon are two silver-silver chloride electrodes. One electrode is an internal potentiometric reference electrode, the other electrode is further coated with an integral water permeable layer, then a pH sensing layer constituting together an internal pH indicator electrode. The electrode pair is further coated with two hydrophilic matrixes containing electrolytes, together constituting the integral internal electrolyte, and then a gas permeable membrane. Thus, the potentiometric gas sensor of this typical example requires seven coating steps onto the conductor elements and their insulating support. This device is wet-up prior to use, then immersed in a test solution containing dissolved carbon dioxide. The gas diffuses through the gas permeable membrane into the integral internal electrolyte layer where it dissolves and changes the pH of the electrolyte. The integral internal electrolyte and the two internal electrodes are electrically isolated from the test solution by the gas permeable membrane. The pH change of the internal electrolyte, which is related to the carbon dioxide concentration, is measured by the voltage between the internal indicator and reference electrode.

Simplifications of the classical two-electrode carbon dioxide sensor design have been disclosed in U.S. Pat. No. 5,496,521. This patent describes a carbon dioxide electrode with no internal reference electrode. The device comprises an indicator pH electrode an integral internal electrolyte layer and an ionophore doped homogeneous gas permeable over-layer. The test solution is electrically connected to the integral internal electrolyte by the ion conduction through the homogeneous, ionophore-doped membrane. The sensor of this construction still needs at least four coating layers on the conductor elements and their insulating substrate. Similarly, U.S. Pat. No. 5,554,272 describes a bicarbonate sensor using a homogeneous gas permeable membrane rendered ion conducting by incorporation of an ionophore.

Polarographic Oxygen Sensor Prior-Art

The dissolved oxygen sensor is exemplary of polarographic gas sensors of the prior-art. U.S. Pat. No. 4,534,356 is one typical example from a large literature of planar dissolved oxygen sensors. In this example, the device consists of a planar insulating substrate with two conductor elements for connection to a measuring circuit. There is a coating of silver, then silver chloride on one conductor element that constitutes a first electrode, the reference electrode or anode. A coating of a catalytic metal film (gold or platinum in this example) applied over the other conductor element constitutes the second electrode, the cathode. The electrode pair is further coated with an integral electrolyte layer consisting of a hydrophilic membrane containing dissolved salts and then a second layer which is a gas permeable membrane (Teflon in this example). Thus, this polarographic gas sensor consists of six coating steps for applying the various layers onto the conductor elements and their insulating support. Another typical example is U.S. Pat. No. 5,246,576. In this device there are anode and cathode metal coatings on a planar substrate, with two over-layers. The first is an integral electrolyte layer comprising a hydrophilic membrane containing salts. The second layer is formed from one or two gas permeable membrane coatings. There are a total of eight coating steps in this device. These devices are wet-up prior to use so that the integral electrolyte immersing the electrode pair already contains water and dissolved salts. In use, these devices are immersed into a test solution containing dissolved oxygen. The gas diffuses through the pas permeable membrane and then diffuses through the integral electrolyte to the cathodic electrode surface where it is electrochemically reduced. The internal electrolyte and the two internal electrodes are electrically isolated from the test solution by the gas permeable membrane. The current flowing between the internal anode and cathode is proportional to the oxygen concentration Modifications to the classical polarographic oxygen sensor design are disclosed in U.S. Pat. No. 5,514,253. This patent describes an oxygen electrode with no internal reference anode. It consists of a cathode coated with an integral electrolyte layer and a gas permeable over-layer. There are openings through the gas permeable over-layer so that the integral electrolyte makes electrical contact with the external test solution well away from the electrode region. This configuration allows the use of an external reference electrode. However, there are still four coating steps required in this example. U.S. Pat. No. 5,078,854 discloses a polarographic oxygen electrode with an integral internal electrolyte and a continuous (homogeneous) gas permeable membrane over-layer. The gas permeable over-layer is rendered appropriately ion conducting by dissolving lipophilic ions into it. As with U.S. Pat. No. 5,514,253, this patent teaches a simplified polarographic electrode with no internal reference electrode. At least three coating steps are required to fabricate this prior-art sensor.

It is thus an essential feature of conventional sensors of the types discussed above that the integral internal electrolyte element is large enough and sufficiently well isolated from the test solution that it behaves as a reservoir which immobilizes the sensor's reagents within it. In these conventional sensors the reservoir's reagent composition thus remains essentially fixed for the duration of a measurement (except in the first few seconds during wet-up of dry stored devices and except for the chemical reaction involving the species to be analyzed whose compositional changes constitute the sensor reaction), and contaminants from the test solution are excluded from and thus at low concentration in this internal electrolyte reservoir. Indeed, it is most often the case that the composition of reagents in the internal electrolyte reservoir element at the electrode surface remains fixed for numerous measurements because these devices have been typically designed to be reusable. In these typical prior-art devices the sensor's internal electrolyte element is completely isolated from the test solution by one or more layers that selectively transport only the species to be analyzed. For example, prior-art dissolved carbon dioxide and oxygen sensors consist of internal electrolyte elements covering the sensors' electrodes and a selectively gas permeable, but electrolyte impermeable over-layer on top of that. In other prior-art devices, where there is direct contact between the internal electrolyte element and the test solution, but the internal electrolyte adjacent the electrode is far removed from the point of contact to the test solution.

For these and other reasons prior-art planar electrochemical sensors have required numerous electrode materials and membrane coatings to achieve the desired functionality. Prior-art planar electrochemical sensors, therefore, are complicated and expensive to produce. In addition, such devices generally still also require at least a single, in-use calibration fluid step to achieve a performance equivalent to laboratory analyzers. Even sensor designs that use micro-fabrication technology (U.S. Pat. Nos. 5,063,081 and 5,514,253 for example) with its high levels of dimensional precision have failed to achieve the standard of performance (reproducible slope and intercept of the response) required for use without a calibration step in a fluidics-free analyzer.

Manufacturers of home use glucose sensors have developed far simpler devices that are manufactured at low cost. Such devices do not require calibration at the point-of-use, but they still require lot-calibrators. However, as is appreciated by those skilled in the art, these devices do not meet the performance requirements of the quantitative laboratory analysis and are classified as semi-quantitative. Thus there remains a significant need to provide electrochemical sensor devices for precise quantitative analysis which are sufficiently simple in design and construction for use as cost-effective unit-use devices.

SUMMARY OF THE INVENTION

It is an object of this invention to provide unit-use electrochemical sensors and their electrode components.

It is a specific object of the invention to provide unit-use salt-bridge reference electrodes and indicator electrodes manufactured as substantially dry reagent devices, which reach their active state after incorporation of water at the point of use.

It is an object of this invention to provide unit-use salt-bridge reference electrodes and indicator electrodes that are used with a single calibrator solution, preferably in a device wherein the electrodes and calibrator are all contained within a single, unit-use housing.

It is a further object of the invention to provide salt-bridge reference electrodes and dissolved gas sensors each constructed with at least a single heterogeneous membrane. The heterogeneous membrane has the property that it supports rapid gas and water vapor transport through a hydrophobic gas permeable compartment and constrained electrolyte transport through a hydrophilic compartment.

These and other objects are met in a device comprising an electrode for use in an electrochemical sensor for the analysis of an aqueous sample, comprising an electric conductor; an insulating layer on the conductor, the insulating layer having a through-going aperture defining an electrode region; and at least a heterogeneous membrane layer having gas and electrolyte conducting properties for direct contact with the sample, the heterogeneous membrane being in contact with the insulating layer over the electrode region and extending through the aperture into electrical contact with the conductor. The term 'electrode' as used in this description defines an electric conductor layer covered by an insulator layer except for an electrode region in which the conductor layer is exposed. The electrode region can be located at an edge of the insulator layer or within the insulator layer, in the form of a throughgoing aperture in the insulator layer.

Carbon dioxide and oxygen sensors comprising a heterogeneous membrane of the invention now require only a single electrode rather than the electrode pair in the classical design for sensors of this type. Because the heterogeneous membranes of gas sensors of the current invention are electrically conducting through their hydrophilic compartment an external reference electrode can be used with them.

The heterogeneous membrane of this invention is a formulation that comprises an intimate admixture of at least two compartments, a hydrophilic compartment that supports constrained transport of electrolyte salts and other non-volatile species and their chemical reactions and a hydrophobic compartment that supports rapid gas and water vapor transport. Such a heterogeneous membrane in accordance with the invention can be used as an element of a unit-use sensor of very simple construction.

In a first embodiment of an electrode with a heterogeneous membrane of the invention, the electrode comprises a single conductor element for connection to a measuring circuit which conductor is coated by a first hydrophilic reservoir layer which in turn is coated by a second heterogeneous membrane layer. The heterogeneous membrane provides the dual electrolyte and gas-conducting properties required for proper device function. In this embodiment of the invention the first hydrophilic layer is in contact with the electrode, it is initially substantially dry, and after wet-up during the use of the device, it constitutes an internal electrolyte reservoir that contains the reagents required for the electrode reaction. The heterogeneous membrane preferably supports rapid water vapor transport through its hydrophobic compartment, to enable the wet up of the internal electrolyte reservoir. The heterogeneous membrane also enables electrical contact between the internal electrolyte reservoir and the test solution by electrolyte transport through its hydrophilic compartment, but the permeation rate through the hydrophilic compartment by electrolytes and other water soluble non-volatile species is preferably sufficiently slow that the internal reservoir is effectively isolated from the external test solution during the time course of the measurement.

In another embodiment, the device consists of a single conductor element for connection to a measuring circuit which conductor is coated with a heterogeneous membrane. The heterogeneous membrane preferably provides within a single element the internal electrolyte reservoir and the constrained electrolyte transport and rapid gas transport properties required for proper device function. In this preferred embodiment the heterogeneous membrane's initially substantially dry hydrophilic compartment, when wet up during use of the device, serves as the internal reagent reservoir. The heterogeneous membrane's hydrophobic compartment provides for rapid water vapor transport to wet-up the hydrophilic compartment up to the electrode surface.

By contrast with the design of conventional electrodes of the prior art, in electrodes of the current invention it is not necessary to completely isolate the electrode's internal electrolyte reservoir from the test solution. In preferred embodiments, the reagent composition of the hydrophilic compartment of the heterogeneous membrane, (or of the optional additional internal reservoir in close proximity to the electrode surface) actually can change over time during the operation of the device. For example, reagents may diffuse out of the heterogeneous membrane into the test solution or contaminants permeate into the membrane from the test solution. In devices of the invention it is sufficient only that the transport of reagents or contaminants through the membrane be sufficiently constrained that, after wet up, the internal reservoir's composition changes only slowly and it then functions as if it was effectively isolated. Surprisingly, even though numerous elements that are typically necessary to be present in prior-art devices have been omitted from the simplified devices of this invention, the important characteristics defining quantitative sensing performance are retained: the invented electrodes exhibit fast wet-up (important when the device is stored dry prior to use), at least reproducible response intercepts if they are polarographic devices and at least reproducible response slopes if they are potentiometric devices, and the devices exhibit freedom from interferences. Thus these very simple devices of the invention can be incorporated into an analyzer requiring only a single in-use calibration fluid.

This invention teaches compositions of heterogeneous membranes and methods of measurement using electrodes incorporating heterogeneous membranes that can tolerate some loss of their reagents into the test solution or acquire some contaminants from the test solution during use. Specifically this invention teaches the range of desirable transport properties of heterogeneous membranes to achieve electrodes usable in accurate and quantitative electrochemical measurements. It is desired that the membrane's diffusion coefficient of water vapor (and carbon dioxide or oxygen for the respective gas sensors) should be at least 10 times faster than the constrained diffusion of aqueous electrolytes and other water soluble species, and preferably greater than 50 times faster. More specifically it is preferred that gas and water vapor diffusion occurs at greater than $1 \times 10^{-8}$ $cm^2 sec^{-1}$ and electrolyte salt diffusion at less than $1 \times 10^{-7}$ $cm^2 sec^{-1}$.

This invention teaches heterogeneous membranes formulated using gas and water vapor permeable polymers such as polydimethylsiloxane, acrylated siloxanes, polyurethanes and the like, in intimate admixture with an interpenetrating hydrophilic compartment typically comprising hydrophilic polymers, electrolyte salts and other reagents. The intimate admixture of the resultant heterogeneous membrane provides a rapid gas and water vapor transport path through the hydrophobic compartment and a tortuous transport path for electrolyte salts through the hydrophilic compartment.

Preferred heterogeneous membranes including an intimate admixture of hydrophobic and hydrophilic compartments achieve the necessary constrained electrolyte transport when they have less than 5% by volume of the hydrophilic compartment.

A preferred embodiment of a salt bridge reference electrode comprises a heterogeneous membrane of the invention having an internal reservoir including at least a dry redox salt but optionally other additional salts which together form an approximately equi-transferrent electrolyte in the reservoir when it is wet up.

A preferred embodiment of a potentiometric carbon dioxide electrode includes a heterogeneous membrane in accordance with the invention and an internal reservoir containing at least dry bicarbonate salt and a pH sensitive redox salt but optionally also carbonic anhydrase, with the bicarbonate at a dry loading level so that the reservoir achieves a bicarbonate concentration larger than 25 mM but less than 800 mM after it wets up.

A preferred embodiment of a polarographic oxygen electrode in accordance with the invention comprises a heterogeneous membrane of the invention whose hydrophobic compartment has an oxygen permeability less than about $6 \times 10^{-13}$ mole $cm^{-1} s^{-1} atm^{-1}$.

To better achieve the desired transport properties of the heterogeneous membrane this disclosure teaches membranes cast from emulsions in which one of the constituent components is cross-linked to further depress the salt diffusion coefficient through the hydrophilic compartment. This can be achieved in one of two ways. This disclosure shows that the salt diffusion coefficient and the diffusion coefficient of other non-volatile species through the hydrophilic compartment of a heterogeneous membrane can be engineered to be sufficiently low when the membrane's hydrophilic compartment comprises a polymer with photo-reactive pendant groups which can cause cross-linking of the hydrophilic polymer upon photo-irradiation of the cast membrane. In an alternative approach the membrane's hydrophobic compartment can be cross-linked by photo-irradiation of the cast membrane when the hydrophobic compartment contains photo-cross-linking entities. Still another approach is to cross-link both the hydrophilic and the hydrophobic compartment. The desired result in all cases is that the hydrophilic compartment is rapidly wet up by water vapor transport through the hydrophobic compartment, thus achieving the required water content in the internal reservoir for proper electrode function, but is sufficiently constrained from swelling by the above recited cross-linking that it retains a low salt diffusion coefficient.

The invention teaches methods of preparation of heterogeneous membranes from oil-in-water emulsions.

This invention teaches the fabrication of an electrode comprising a heterogeneous membrane in which the membrane material in a fluid is deposited onto a planar substrate using a micro-dispensing method.

A preferred and surprisingly simple device and its manufacturing process results when the heterogeneous membranes of this invention are fabricated by micro-dispensing of a casting fluid containing membrane components onto low cost smart card-type electrode modules (as disclosed in U.S. Pat. Publ. No. 2002-0179444-A1 and in co-pending patent application U.S. patent application Ser. No. 10/307,481). These substrates are laminations of gold-coated copper with epoxy foils, the epoxy foil being die-cut with through-going holes at the electrode locations, heterogeneous membranes being micro-dispensed into the epoxy holes of the electrode module. The modules' electrode surface material is gold. Because electrode modules are supplied on a web as a 35 mm strip, a printing process in which the membranes are dispensed onto the modules while still on the web is particularly advantageous, being rapid, simple and low cost. Multiple different membranes, including heterogeneous membranes for reference electrodes, carbon dioxide and oxygen sensors of this invention as well as other membrane types such as those for ion selective electrodes and enzyme sensors, can be micro-dispensed onto a module comprising multiple electrode locations to fabricate a low cost sensor array.

BRIEF DESCRIPTION OF THE DRAWINGS

The invention will now be further described by way of example only and with reference to the attached drawings, wherein.

DETAILED DESCRIPTION OF THE PREFERRED EMBODIMENTS

Heterogeneous Membrane Electrodes

Figure 1A:
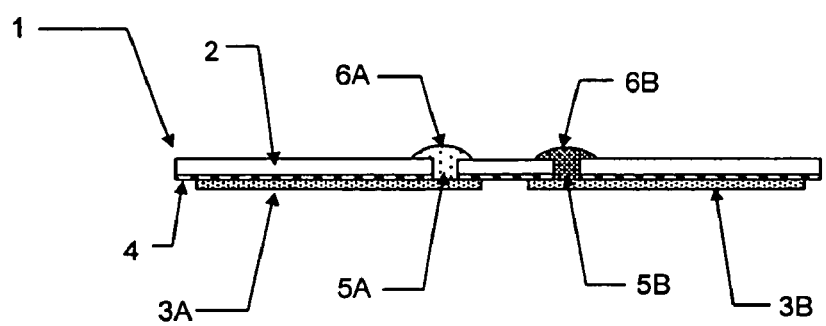
FIG. 1A is a cross-section through a preferred embodiment of an electrode in accordance with the invention, including a heterogeneous membrane coating of an electrode of a laminated foil electrode module.

The heterogeneous membranes according to this invention are materials consisting of an intimate admixture of two components. The first is a hydrophobic gas permeable material component, the second is a hydrophilic electrolyte conducting component. The heterogeneous membrane comprises these two components as physically separate compartments within the membrane. The intimately admixed hydrophobic and hydrophilic compartments comprising the membrane are a dispersion of interpenetrating regions of micron or submicron size of each component, the resulting membrane material having interpenetrating networks of the two compartments. In a preferred composition, the hydrophobic component is present in large excess by volume over the hydrophilic component. The preferred transport property of the heterogeneous membrane of the invention is that the membrane diffusion coefficient for particular gases through the hydrophobic compartment (water vapor for wet-up of all sensor types, oxygen or carbon dioxide for gas sensor membranes) is significantly larger than the membrane diffusion coefficient of species dissolved in the water (ions and neutral non-volatile molecules) contained within the hydrophilic compartment. We have found that sensors can be made with adequate performance attributes when the ratio of these diffusion coefficients is about 10, but preferably the ratio should be at least 50 and better still greater than 100.

It is generally the case that prior to incorporation of water into a dry reagent electrochemical sensor such as the ones of this invention 1. The device exhibits significant noise. Absent water, the bulk membrane components of the device are not yet sufficiently ion conducting, and their electrical resistance is large. 2. The electrode potentials and response slopes of potentiometric electrodes are erratic and vary rapidly over time. Prior to wet-up, electrochemical reactions at electrode interfaces are slow and the electrode potential is said not to be well poised. 3. Polarographic devices exhibit low electrode current and large capacitive transient currents prior to wet-up. Consequently there is an initial time period in which a dry reagent electrochemical sensor should be immersed in an aqueous solution during which time period the device absorbs water prior to achieving its functioning state as a sensor. This is called the wet-up time.

Wet-up of heterogeneous membranes of this invention is by water diffusion as vapor through the gas permeable hydrophobic compartment and then by rapid partitioning from the gas permeable compartment into the hydrophilic compartment within the heterogeneous membrane. The hydrophobic compartment preferably includes a polymer chosen for its large water vapor permeation rate, so that the wet-up step is fast.

Hydrophobic polymers with large water vapor transmission rates are known in the art. Examples, which are typically elastomeric materials include polysiloxanes, polyorganophosphazenes, poly-1-trimethyl-silyl-1-propyne and poly-4-methyl-2-pentyne, polyisoprenes, polybutadienes and polyurethanes. The hydrophobic compartment of the membrane can be a liquid polymer comprised of non-cross-linked polymer or it can be a solid prepared from the liquid by addition of cross-linking agents. The hydrophilic compartment of the admixture of the heterogeneous membrane preferably includes one or more of the following: emulsifiers, hydrophilic polymer binder, optional cross-linkers of the hydrophilic polymer, electrolyte salts and other optional dissolved components depending on the sensor. Hydrophilic polymers are well known in the art. Examples include polyvinylalcohols, polyhydroxymethacrylates, polyacrylamides, polysaccharides, cellulosic polymers and gelatins. Methods of cross-linking hydrophilic polymers also are well known in the art. Other optional constituents of the hydrophilic compartment include catalysts, redox agents, buffers and surfactants that will be incorporated into the membrane upon preparation.

Heterogeneous membranes in accordance with the invention are preferably prepared by casting from solutions and suspensions of the intimately admixed membrane materials in volatilizable solvents. Membranes can be cast from two types of casting fluids 1: from an aqueous casting-solution containing dissolved hydrophilic components and the hydrophobic component either as a dispersion of suspended micron or sub micron sized solid particles of the hydrophobic polymer resin or as an emulsion of suspended liquid hydrophobic polymer or monomer: a so-called oil-in-water emulsion. The emulsion may comprise a liquid suspension of a polymer resin dissolved in a hydrophobic solvent or it can be a solvent-free liquid polymer or monomer. Monomers or low molecular weight liquid precursors in the suspension can be cross-linked into a solid hydrophobic polymer membrane upon casting if the hydrophobic polymer contains reactive groups that can cross-link, or by addition of appropriate cross-linking additives to the emulsion.

2: from a non-aqueous casting solution containing dissolved hydrophobic polymer and the hydrophilic component dissolved in water in an emulsion with the non-aqueous solvent: a so-called water-in-oil emulsion.

Casting membranes containing solid suspensions are possible, but not preferred because they typically will form membranes with air pores. The preferred method of the invention uses oil in water emulsions. Siloxanes, particularly polydimethylsiloxane (PDMS) or derivatives of PDMS comprising reactive pendant groups, polyurethanes and polyurethane derivatives, epoxies and derivatives with active pendant groups have been used for heterogeneous membrane preparations. These materials have been favored because they are widely used in industry and thence readily available.

In principle, any method of deposition of a coating from a volatilizable liquid is feasible. The heterogenous membrane can be cast onto an electrode using any of the methods known in the art such as dispensing through a nozzle, transferring a drop onto the electrode from a solid tip, spin coating, dip coating, spray coating, screen printing and the like. Pin-transfer and nozzle micro-dispensing techniques are preferred.

Upon casting of the membrane from the casting fluid there results a membrane in which the intimate admixture of the hydrophilic and hydrophobic components of the casting fluid is retained during the drying process. The intimately admixed hydrophobic and hydrophilic compartments of the cast membrane are a dispersion of regions of micron or sub-micron size of each component. Depending on the specific conditions of membrane drying, the dispersion of the hydrophilic (hydrophobic) regions may comprise a dispersion of individual isolated particles, or particles that are partially or completely coalesced into continuous interconnected regions, in which case the two component phases form a pair of continuous interpenetrating networks. In either event the heterogeneous membrane comprises an intimate admixture of two compartments: a first hydrophobic compartment which is a network of interconnected or partially interconnected channels of hydrophobic material through which a gas may be transported and whose channel cross-section is preferably of the order of a few micrometers or less, and a second hydrophilic compartment which is a network of interconnected or partially interconnected channels of hydrophilic material through which an electrolyte may be transported and whose channel cross-section is also preferably of the order of a few micrometers or less.

The specific device dimensions and composition of the heterogeneous membrane element will be different for each of the electrode types encompassed by this invention These will be described in more detail in the following sections.

Devices of this invention encompass sensors that function as potentiometric salt bridge reference electrodes, and potentiometric and polarographic gas sensors, but the inventor clearly contemplates the extension of these design principles to other sensor types such as enzyme electrodes.

Figure 1B:
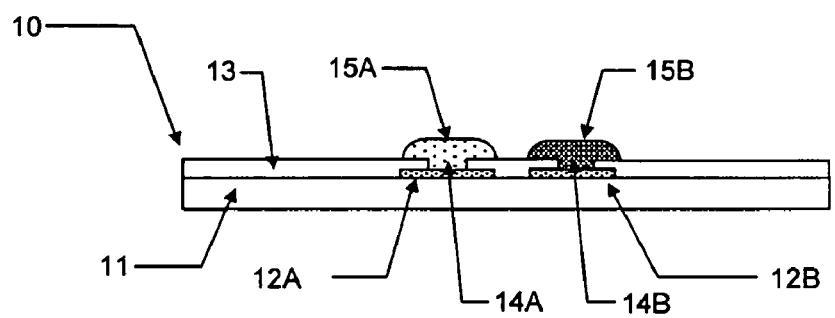
FIG. 1B is a cross-section through an embodiment of an electrode in accordance with the invention, including a heterogeneous membrane coating of an electrode formed on an insulating substrate.

All of the various principal electrode types achievable with the heterogeneous membrane technology of the current invention are depicted in the preferred embodiment of the invention shown in FIG. 1A and an alternative embodiment shown in FIG. 1B. In these figures the specific compositions and dimensions of the elements will depend on the specific electrode type. As will be apparent from the following detailed descriptions of each of the different electrode types, the composition, structure and dimensions of the membranes 6A, 6B determine the functional properties of the respective electrode.

FIG. 1A depicts the preferred laminated foil electrode embodiment, while FIG. 1B depicts a coated electrode on an insulating substrate. Both figures illustrate a pair of electrodes to show how multiple electrodes can be produced on a single foil-type electrode module or on a single insulating substrate. It is clearly contemplated in this invention that there could be numerous different combinations of electrodes on a single module as determined by the test application. For example a test device for blood gases (pH, dissolved carbon dioxide and dissolved oxygen) would consist of an array of 4 electrodes on a module (indicator electrodes for pH and the two dissolved gases and a common salt-bridge reference electrode) and a fifth grounding electrode. A glucose test device would be an array of two electrodes on a module and so on.

The laminated foil embodiment of FIG. 1A shown in cross-section includes an electrode module with a pair of electrodes, as described in detail in U.S. Pat. Publ. Nos. 2002/0179444A1, 2003/0148530A1 and co-pending U.S. patent application U.S. patent application Ser. No. 10/307,481. The electrode module includes an insulator foil 2 laminated with a metal foil formed into two elements 3A, 3B and optional adhesive 4 therebetween. Apertures 5A and 5B extend through the insulator and define the position of the two electrodes. Coatings 6A and 6B are applied over the apertures and extend thereinto, with overlap onto the insulator (contacting at least the vertical wall of the insulator in the aperture or even beyond onto the planar insulator surface perimetric to the aperture). The coatings 6A, 6B are in electrical contact with the metal foil elements at 3A, 3B.

The coated insulating substrate embodiment of an electrode module 10 is shown in cross-section in FIG. 1B including a pair of electrodes. A planar insulating substrate 11 supports a metal film formed into two elements 12A, 12B coated by an insulating over-layer 13. Apertures 14A and 14B extend through the insulating over-layer and define the respective position of the two electrodes. Coatings 15A and 15B extend into the apertures, overlap onto the insulating over-layer, and make contact to the conductors 12A, 12B.

There are two principal variants of the membrane configuration of the devices of FIGS. 1A and B. In the first variant there is only a single heterogeneous membrane overlaying the conductor. In the second variant there is an internal hydrophilic reservoir layer coating the conductor, then a second over-layer of a heterogeneous membrane. In either variant, coatings 6A and 6B of FIGS. 1A and 15A and 15B of FIG. 1B comprise one or more membrane elements with at least one heterogeneous membrane element according to this invention.

Heterogeneous Membrane Transport Properties

Consideration of the membrane's transport properties is needed to better understand the design rules for the selection of materials and composition of the heterogeneous membrane according to this invention. To model the transport properties of the heterogeneous membrane one needs to know the transport properties of the materials of its transport compartments and the nature of their admixture, particularly the relative volume of the hydrophobic and hydrophilic compartments, the characteristic dimensions of the hydrophilic compartment's transport paths and the tortuosity of the species transport networks created when the two components are intimately admixed.

The tortuosity of a membrane's transport path describes the reduced rate of species diffusion relative to diffusion through a slab of pure material. In a heterogeneous membrane of this invention the tortuosity can be modeled by the increased path length for transport of a continuous path or by the reduced rate of particle transport from isolated islands within a discontinuous path. Both such models of transport are well known in the art of membrane transport.

A heterogeneous membrane of this invention is a slab of geometric area A and geometric thickness L and volume V=AL which comprises a volume $V_G$ of a gas (water vapor) permeable polymer of the hydrophobic compartment and $V-V_G=V_H$ of a hydrophilic compartment.

The heterogeneous membrane has two transport paths through its thickness. There is a first transport path for gas and water vapor through the hydrophobic polymer compartment. The hydrophobic polymer is a material characterized by a gas (water vapor) solubility $S_G$ ($S_W$) moles cm$^{-3}$atm.$^{-1}$ and a gas (water vapor) diffusion coefficient $D_G$ ($D_W$) cm$^2$sec$^{-1}$. When the membrane is contacted by an adjacent liquid water phase the membrane absorbs water as vapor through the hydrophobic compartment, coming to an equilibrium water content of $S_G P$ moles of water per cm$^3$ of the hydrophobic compartment where P in atmospheres is the saturated vapor pressure of water. The hydrophobic gas/water vapor transport path is characterized by an effective area $A_G$, and an effective length $L_G$. The ratio $L_G/L>1$ characterizes a longer transport path for gaseous permeant than the geometric thickness. The ratio $(L_G/L)^2=\tau_G$ characterizes the tortuosity of the gas permeant path. For a heterogeneous membrane in which the predominant volume component is the hydrophobic compartment, $V_G/V>>0.5$, the tortuosity will be in the range $1<\tau_G<2$. The effective diffusion coefficient of gas/water vapor through the gas permeable path of the heterogeneous membrane is $D_{G,M}$ given by $D_{G,M}=D_G/\tau_G$ where the effective diffusion coefficient relative to the membrane is less than the diffusion coefficient in a slab of the pure hydrophobic polymer $D_G$ by the tortuosity factor $\tau_G$. As noted, we have preferred polysiloxanes and derivatives thereof and polyurethanes and derivatives thereof as a preferred gas permeable material because of their high water vapor permeation rate. Published data for gas solubility and diffusion coefficient and permeability for these polymers and others are shown in Table I. Published data for a given class of materials is quite variable because it depends on the degree of cross-link of the material, permeability being higher for lower cross-linked elastomers. Polydimethylsiloxane has the highest permeability and diffusion coefficient of the common elastomeric polymers (poly-1-trimethyl-silyl-1-propyne is reported to be even higher.)

TABLE 1

| polymer | Gas | D cm$^2$ sec$^{-1}$ | S mol · cm$^{-3}$ atm$^{-1}$ | P = DS mol · cm cm$^{-2}$ sec$^{-1}$ atm$^{-1}$ |
|---|---|---|---|---|
| polydimethylsiloxane | H$_2$O | 1 × 10$^{-5}$ | 1 × 10$^{-3}$ | 1 × 10$^{-8}$ |
| polyether-urethane | H$_2$O | | | 3 × 10$^{-8}$ |
| polyester-urethane | H$_2$O | | | 4 × 10$^{-9}$ |
| polybutadiene | H$_2$O | | | 2 × 10$^{-9}$ |
| polyisoprene | H$_2$O | | | 8 × 10$^{-10}$ |
| polydimethylsiloxane | CO$_2$ | 1.1 × 10$^{-5}$ | 6 × 10$^{-5}$ | 7 × 10$^{-10}$ |
| polyether-urethane | CO$_2$ | | | 1 × 10$^{-10}$ |
| polyester-urethane | CO$_2$ | | | 6.1 × 10$^{-12}$ |
| polybutadiene | CO$_2$ | 1.1 × 10$^{-6}$ | 4 × 10$^{-5}$ | 4.7 × 10$^{-11}$ |
| polyisoprene | CO$_2$ | 1.3 × 10$^{-6}$ | 4 × 10$^{-5}$ | 5.2 × 10$^{-11}$ |
| polydimethylsiloxane | O$_2$ | 2 × 10$^{-5}$ | 1.5 × 10$^{-5}$ | 3 × 10$^{-10}$ |
| polyether-urethane | O$_2$ | | | 1 × 10$^{-11}$ |
| polyester-urethane | O$_2$ | | | 4 × 10$^{-13}$ |
| polybutadiene | O$_2$ | 1.5 × 10$^{-6}$ | 4 × 10$^{-6}$ | 6.5 × 10$^{-12}$ |
| polyisoprene | O$_2$ | 1.7 × 10$^{-6}$ | 5 × 10$^{-6}$ | 7.9 × 10$^{-12}$ |

A second transport path for electrolyte salts and non-volatile molecules is through the hydrophilic compartment after it has wet up. The hydrophilic compartment is characterized by a solubility of water $S_H$ moles cm$^{-3}$atm.$^{-1}$. When equilibrated with water at a temperature T there are $S_H P$ moles of water per cm$^3$ of the hydrophilic compartment where P in atmospheres is the saturated vapor pressure of water at temperature T. The transport path is characterized by an effective area $A_H$, and an effective length $L_H$. The ratio $L_H/L>1$ characterizes a longer transport path than the geometric thickness. The ratio $(L_H/L)^2=\tau_H$ characterizes the tortuosity of the hydrophilic path. When the amount of hydrophilic component in the heterogeneous membrane is large, the hydrophilic compartment comprises continuous connected conduction paths within the heterogeneous membrane and $\tau_H$ will be on the order of unity. When the amount of hydrophilic component in the membrane is small ($V_H/V<<0.5$), the hydrophilic compartment's paths are tortuous or even partially discontinuous and $\tau_H$ will be large, and in the limit of a very small volume fraction of hydrophilic component, $\tau_H$ approaches infinity and there is no longer a continuous hydrophilic conduction path through the membrane.

The hydrophilic compartment is further characterized by a model of water-containing micro-capillary pores contained within the hydrophilic matrix. The volume of aqueous electrolyte in the hydrophilic compartment is $V_E$, the volume of the dry other hydrophilic compartment's constituents being $V_H$–$V_E$. At equilibrium after wet up of the membrane, $V_E/V_H=S_HP/0.055$, assuming 0.055 moles of water occupy 1 $cm^3$. The electrolyte transport path within the hydrophilic compartment is characterized by an effective area $A_E$ and an effective length $L_E$. The ratio $L_E/L_H>1$ characterizes a longer transport path for electrolyte diffusant through the pores of the hydrophilic compartment than the hydrophilic compartment's path length. The ratio $(L_E/L_H)^2=\tau_P$ characterizes the tortuosity of the electrolyte pores relative to the hydrophilic path. It is well known in the art of hydrophilic polymer gels that $\tau_P$, the tortuosity of the electrolyte path through the pores of a hydrophilic polymer matrix, can be very large depending on the equilibrium water content of the matrix (also related to the swelling factor). The smaller the water content the larger the tortuosity, so that typically $1<\tau_P<1000$ when $1>V_E/V_H>0.01$. Consequently it is possible to formulate hydrophilic matrixes where the water content is of the order of a few percent of the volume of the hydrophilic matrix and the diffusion coefficient of aqueous diffusants in the hydrophilic matrix is up to 100 or more times lower than the diffusion coefficient in water. (see for example Hydrogels in Medicine and Pharmacy, CRC Press, N. A. Peppas ed., Vol 1 1986). For diffusion of small molecules through a hydrophilic polymer containing $V_E/V_H$ volume fraction of water, the diffusion constant of a salt through the hydrophilic compartment $D_H$ is less than the diffusion coefficient in water $D_W$ by a factor given by $$\frac{D_H}{D_W} = \frac{1}{\tau_p} = e^{N\left(1-\frac{V_H}{V_E}\right)} \qquad \text{Equation 1}$$

where N is a constant close to unity (see for example H. Yasuda et al. "Permeability of Solutes through Hydrated Polymer Membranes" in Die Makromolekulare Chemie 118 (Nr. 2858), (1968) p 19-35).

The constraint of water uptake and resultant swelling of the hydrophilic compartment of the wet-up heterogeneous membrane is thus often necessary to achieve the desired low salt diffusion coefficient, and can be achieved in one of two ways: by cross-linking of the hydrophilic matrix or by cross-linking of the hydrophobic matrix, both techniques providing the elastic compressive forces that counteract the swelling of the hydrophilic compartment during wet up. We demonstrate both approaches in this disclosure. The literature of hydrophilic polymers (of which the two above citations are typical) provides numerous examples of chemical cross-linking methods to achieve hydrophilic polymers with different amounts equilibrium water uptake and consequently different salt diffusion coefficients. The literature of gas permeable hydrophobic polymers too, contains numerous examples of their cross-linking chemistry.

Combining the tortuosity of the electrolyte path in the hydrophilic matrix and the tortuosity of the hydrophilic matrix path within the heterogeneous membrane gives the total tortuosity of the electrolyte path with respect to the membrane as $(L_E/L)^2=\tau_P\tau_H=\tau_E$. The effective diffusion coefficient of a species dissolved in the pore water of the hydrophilic compartment of a heterogeneous membrane is $D_{E,M}$ given by $D_{E,M}=D_E/\tau_E$ where the effective diffusion coefficient relative to the heterogeneous membrane is less than the diffusion coefficient in a slab of pure aqueous electrolyte $D_E$ by the tortuosity factor $\tau_E$.

As discussed, the transport of gas and water vapor through the heterogeneous membrane is primarily by diffusion through the gas permeable compartment and then by partitioning from the gas permeable compartment into the intimately admixed hydrophilic compartment within the membrane. The partitioning of water between the hydrophobic and hydrophilic compartments' pores can be assumed to be an equilibrium process when the transport of water across the hydrophobic/hydrophilic pore boundary is rapid compared to transport along the pore through the thickness of the membrane. The characteristic distance of hydrophobic to hydrophilic pore transport is on the order of the pore size of the admixture (on the order of a few micrometers or less) which is small compared to the membrane thickness (on the order of 100 micrometers). When transport of water from the hydrophobic compartment to the hydrophilic compartment is slower, such as when the characteristic pore size of the heterogeneous admixture is large, an additional time constant is introduced to the water absorption kinetics. When the water uptake into the hydrophilic pore is a slow process, then too there is an additional time constant in the water absorption kinetics.

The transport of electrolyte is through the water-filled capillary pores within the hydrophilic compartment only.

To better understand the required range of transport properties of the heterogeneous membranes of this invention we have performed simulations of the invented electrodes' response characteristics using a finite difference numerical method. With this method we solved the equations describing the simultaneous transport of the various species through the heterogeneous membrane. The results of this simulation are the species' concentrations (water, ions other solutes and gases) within the membrane versus position and time. These concentration values are then used to calculate the electrical responses of electrodes using heterogeneous membranes of this invention. These numerical simulations and the data from exemplar heterogeneous membrane electrodes made in accordance with this invention are presented below to teach how to best practice the invention.

Diffusion of Water into Heterogeneous Membranes

We have computed the wet up of heterogeneous membranes as follows: First we calculate the time and position dependence of water diffusing as the vapor into the membrane through the hydrophobic compartment. The numerical solution of the transport equations used an initial condition of 0.01 $S_W$ moles $cm^{-3}$ of water corresponding to the initial equilibrium water content of a hydrophobic polymer with water solubility $S_W$ moles $cm^{-3}atm.^{-1}$ initially stored in an ambient of 0.01 atmospheres of water vapor (corresponding to normal room air at 23° C. and 40% RH). The solubilities and diffusion coefficients used in these calculations are those shown in Table 1 for highly water vapor permeable polymers. The amount of water in the hydrophilic compartment is obtained by computing the equilibrium partitioning between the hydrophobic and hydrophilic compartments (assuming a value for the equilibrium water uptake of the hydrophilic compartment, this being related to the equilibrium swell factor determined by the degree of cross-linking of the membrane). The amount of water versus time at the inner membrane surface at the electrode is thus obtained. The time to 95% water uptake at the inner surface, $t_{95}$, is then obtained from the computed time transient.

The results of this computation are: the wet-up time increases linearly with the equilibrium amount of water taken up by the membrane: the wet-up time increases as the square of the membrane thickness. These data can be reduced to a single equation that engineers can use to calculate wet up time for a particular membrane formulation.

$$t_{95} = \frac{L^2}{P_W}\left(\frac{V_E}{V} + 1.2 S_W\right)$$ Equation 2

$P_W$ being the hydrophobic polymer's water vapor permeability ($P_W=D_W S_W$) in units of mole-cm/cm$^2$-sec-atm., L being the membrane thickness in cm., $S_W$ being the hydrophobic polymer's water vapor solubility in units of mole/cm$^3$-atm.

Typical membrane compositions according to this invention have a volume fraction of the hydrophilic compartment between 1% and 5% i.e., 0.01(1%)<$V_H$/V<0.05(5%), and a water uptake into the hydrophilic compartment of between 1% and 20% volume fraction of the hydrophilic compartment i.e., 0.01(1%)<$V_E$/$V_H$<0.2(20%). The total volume fraction of water in the wetted-up membrane is accordingly in the range 0.0001(0.01%)<$V_E$/V<0.01(1%).

A heterogeneous membrane formulated with polydimethylsiloxane, whose water vapor solubility is 1×10$^{-3}$ moles cm$^{-3}$atm.$^{-1}$ and diffusion coefficient is 1×10$^{-5}$ cm$^2$sec$^{-1}$, at a typical thickness of 0.005 cm. absorbing 1% water has a wet-up time of $t_{95}$=28 seconds calculated from equation 2. Such a formulation will still wet up quickly ($t_{95}$=90 secs) even when it takes in 3% water, or if it takes in 1% water and it is 0.009 cm thick.

A heterogeneous membrane formulated with a less water vapor permeable polymer, say one whose water vapor solubility is only 1×10$^{-4}$ moles cm$^{-3}$atm.$^{-1}$ and diffusion coefficient is 1×10$^{-8}$ cm$^2$sec$^{-1}$, must be formulated with a smaller water absorption capacity or it must be made thinner to also wet-up rapidly. For example, with 0.1% water uptake and 0.0028 cm thickness equation 2 predicts a wet-up time of $t_{95}$=88 seconds In performance tests of experimental heterogeneous membrane electrodes described below we have experimentally confirmed the finite element simulation's predictions of the wet-up time. We have used the above relations to determine the useful composition range and membrane thickness for rapid wet-up, being defined as $t_{95}$ less than about 100 seconds.

Details of Membrane Cocktail Preparation

Membrane cocktails (the formulation used for printing membranes) were generally formulated as oil-in-water emulsions. The general procedure for preparation of an emulsion was as follows:

1. The components of the hydrophilic compartment were first pre-mixed by dissolving them in an aqueous solution. These components include the hydrophilic binder (polyvinyl alcohol or another hydrophilic polymer) or an emulsifier, and salts.

2. Next the components of the oil phase were pre-mixed. These include the hydrophobic polymer (typically a low to medium molecular weight polymer) and optional cross-linkers.

3. The oil and water components were mixed to a smooth blend avoiding foam formation.

4. The oil-water blend was emulsified as follows
the best results were obtained when emulsification was performed on ice
24 mL batches of emulsion were prepared in an 8 mL vial using an 8 mm rotor equipped on either an IKA Ultraturrax T25 (500 watt) for viscous formulations or IKA Ultraturrrax T8 (100 watt) blender for non-viscous formulations.
The actual emulsification protocol depended on the formulation, but a typical protocol employed was one where the shear rate is gradually increased during the emulsification process, i.e. 1-2 minutes at 6,000-8,000 rpm, 1-2 minutes at 15,000 rpm and 1-2 minutes at 24,000 rpm.
Best emulsification was obtained when a high viscosity aqueous component was formulated using a relatively higher concentration of dissolved hydrophilic polymer solids.
A desirable emulsion according to the above procedure achieved a high specific surface area of about 2.5 m$^2$/mL. This corresponds to particle dimensions of less than 1 micrometer. Larger particle size emulsions are not preferred because: the emulsion isn't stable over time; the hydrophilic compartment of the cast membrane is not sufficiently tortuous; wet-up is not uniform.

5. Cocktails were stored in a stoppered vial (a dark vial for photo-cross-linkable formulations) until membrane printing. Pot life of a properly emulsified formulation is generally weeks, but new batches were typically prepared weekly.

Details of Membrane Printing, Curing and Cross-Linking

Heterogeneous membrane electrodes were fabricated on smart-card type electrode modules. These were designed to our specified electrode geometries and purchased from a vendor of smart card modules. The modules comprised an epoxy foil body approximately 1 cm×1 cm and 0.01 cm in thickness with one side laminated with a 0.0015 cm copperfoil which was plated with gold. The metal foil had been photo-formed into 8 contact pads in a geometry similar to the ISO standard for smart card modules. There were eight 0.7 mm diameter holes die-cut through the epoxy foil in regions above the contact metal.

The modules were used for preparation of electrodes as received from the vendor. Membranes were printed by the pin-transfer printing technique as well as micro-dispensing from a fine nozzle. The nozzle dispense technique is preferred because it is more appropriate for scaling to high volume. In the pin transfer method a metal pin was immersed into the print cocktail to acquire a charge of print material. The pin with print material was then transferred to the surface of the module in the region of a hole in the epoxy. The print charge was deposited over the hole when the pin with its print material was brought into contact with the module surface. In the nozzle dispense technique the print cocktail was loaded into the barrel of a syringe dispense tool. The syringe tip was 27 to 32 gauge stainless steel. During printing the syringe tip was located in close proximity over the print hole in the module's epoxy and a controlled volume of fluid was dispensed into the hole by applying a pressure to the fluid in the syringe barrel. Print cycle-time was under 1 second. The applied pressure required to deliver a known volume of fluid depended on the viscosity of the cocktail.

The wet thickness of the print was typically about 0.02 to 0.05 cm and the diameter about 0.1 cm.

Wet printed membranes were allowed to air dry at room temperature. Membranes containing photo-cross-linkable components were then flood-exposed to UV from a commercial high intensity UV lamp (EFO Acticure A4000, set at 6 W cm$^{-2}$). The exposure time depended on the specific formulation and the membrane thickness but was typically a few seconds. The dry, cured membranes were soft elastomers with a thickness in the range 0.002 to 0.01 cm, depending on the electrode type.

For test devices we typically printed several electrodes per module with a given cocktail. Modules were stored at room temperature (20-25 C.) and humidity (40-50% RH) prior to testing.

Details of Electrode Testing

Preliminary electrode evaluations were performed on modules mounted in a flow cell. Qualified membrane formulations were then tested on modules assembled into diagnostic cards in a card reader.

For electrodes which were tested in a fluidic cell, the cell comprised a fluidic chamber for introduction of aqueous fluids. The cell consisted of two spaced-apart planar surfaces, one being the electrode surface of the module for test, the other a slab of polycarbonate. The surfaces were spaced apart by a silicone rubber gasket which fluidically sealed the chamber. Fluids were introduced to the chamber through a first inlet pipe and removed through a second outlet pipe each connected through the polycarbonate slab. The contact surface of the module was contacted by a smart-card connector manufactured by Amphenol. There was a silver ground electrode in the inlet pipe and a commercial 3M KCl silver/silver chloride reference electrode (Microelectrodes Inc.) in the outlet pipe. For potentiometric measurements each of the reference electrodes on the array of smart-card electrodes, and the in-line commercial reference electrode was connected to a high impedance source follower amplifier and then to a PC through a data acquisition card. For current-voltage measurements a voltage was applied to the in-line silver electrode and the electrodes on the module were connected to current to voltage converters and then to a PC through a data acquisition card.

For electrodes tested in diagnostic cards, modules with printed electrodes were assembled into diagnostic cards also comprising an on-board calibrator in a sealed pouch. Details of the card construction and operation were previously disclosed in U.S. patent application Ser. No. 10/307,481. Card readers were similar to those disclosed in U.S. Pat. Publ. 2003/0148530A1.

Potentiometric Salt-Bridge Reference Electrode with Heterogeneous Membrane

The principle of operation of heterogeneous membrane salt-bridge reference electrodes of this invention is described in the related application U.S. patent application Ser. No. 10/307,481. Briefly, the hydrophilic compartment of the heterogeneous membrane reference electrode is loaded with an equi-transferent electrolyte (a single salt with equi-mobile ions such as potassium chloride, potassium nitrate or sodium formate for example, or a mixture of salts exhibiting equi-transference of anions and cations) and a redox salt to provide a poised potential at the inner membrane/electrode interface. The '481 patent application gave several examples of heterogeneous membrane reference electrodes that were formulated from commercially available polydimethylsiloxane emulsions.

This disclosure supplements those data with further examples of the technology, particularly as we have extended it to include emulsions that we have prepared in our laboratory.

Reference Electrode Examples

We have investigated several families of formulation, each family denoted in the text below as a numbered series. Formulations are oil in water emulsions from which membranes are cast. The oil phase contains the components of the membrane's hydrophobic compartment, while the water phase contains components of the membrane's hydrophilic compartment. The formulation families are shown in the table below. They are arranged according to whether the membrane's hydrophobic or hydrophilic compartment are cross-linked. Preferably at least one of the compartments is cross-linked to achieve sufficiently long-lived reference electrodes wherein the electrolyte salts of the membrane's liquid junction do not diffuse out too quickly during use, nor do contaminants diffuse in too quickly.

TABLE 2

| Hydrophobic compartment | Hydrophilic compartment | Reference Membrane Formulation # |
|---|---|---|
| Non-crosslinked n/a | Non-crosslinked n/a | I |
| Non-crosslinked Polydimethylsiloxane | Crosslinked SBQ derivatized polyvinyl alcohol | II a |
| Polydimethylsiloxane | Polyvinyl alcohol with ammonium dichromate | b |
| Crosslinked Acrylated siloxane | Non-crosslinked Polyvinyl alcohol | III a |
| Acrylated siloxane | Surfactant | b |
| Urethane acrylic | — | c |
| Aminosiloxane + acrylated siloxane | Surfactant | d |
| Crosslinked Fotecoat emulsion | Crosslinked — | IV a |
| Acrylated siloxane | SBQ derivatized polyvinyl alcohol | b |
| Acrylated siloxane | SBQ derivatized polyvinyl alcohol | c |

We have investigated hydrophilic compartments with polyvinyl alcohol binder or no binder but comprising emulsifying surfactants only. We also show examples of hydrophobic compartments comprising both siloxanes and urethanes.

Formulation IIa

Oil:

1.5 g polydimethysiloxane (Aldrich, 378402, 10,000 cSt)

0.5 g hexamethyldisiloxane (Aldrich, 205389)

Water:

0.06 g polyvinylalcohol (Fluka, 18-88), derivatized with 2.75% (+/−0.25%) SBQ 1.22 g DI water 0.2 g 0.2M potassium chloride solution Derivatization of polyvinylalcohol by SBQ (N-methyl-4-(p-forylstyryl)pyridinium methosulfate, from Esprix Technologies) was performed by us according to procedures described in the literature (for example K. Ichimura, J. Polymer Sci., 22, 2817-2828, 1984)

Formulation IIb

Oil:
1.0 g polydimethylsiloxane (Aldrich, 378402, 10,000 cSt)
0.35 g hexamethyldisiloxane (Aldrich, 205389)

Water:
0.06 g polyvinylalcohol (PolyScience, 49-88)
0.9 g DI water
0.48 g 0.1M ammonium dichromate solution
50 microL 200 mM potassium chloride solution Formulation IIIa Oil:
2.2 g 5% acrylated siloxane (Gelest, UCS-052, 150-200 cSt)
0.06 g α-hydroxycyclohexylphenylketone (Aldrich, 405612)
0.06 g αα-dimethyl-α-phenylacetophenone (Fluka, 38781)

Water:
0.1 g polyvinylalcohol (Fluka, 18-88)
1.9 g DI water
0.1 g 0.1M potassium ferricyanide solution
0.1 g 0.1M potassium ferrocyanide solution We have also made similar formulations using higher percent acrylated siloxanes such as 10% acrylated siloxanes (from Rhodia, Rhodosil R01194, 800 cSt) sensitized with 2.5% by weight of αα-dimethyl-α-phenylacetophenone (Fluka 38781) and 99% (acryloxypropyl) methylsiloxane, sensitized (Gelest, Zipcone UA, 100 cSt). Increasing acrylation above 10% did not improve the membrane performance but resulted in slower wet-up, and we have preferred the low acrylated siloxane formulations.

Formulation IIIb

Oil:
1.0 g 10% acrylated siloxane (Rhodia, Rhodosil R01194, 800 cSt)
0.025 g α-hydroxycyclohexylphenylketone (Aldrich, 405612)
0.025 g α-dimethyl-α-phenylacetophenone (Fluka, 38781)

Water:
0.1 g 75EO-DMS, dimethylsiloxane-75% ethylene oxide copolymer (Gelest, DBE-712)
0.1 g 0.1M potassium ferricyanide solution
0.1 g 0.1M potassium ferrocyanide solution
20 microL 50 mM potassium chloride solution Similar results were obtained with other emulsifying surfactants such as pluronic P123 (from BASF) and carbinol-siloxane Formulation IIIc 2.0 g urethane acrylic emulsion, Joncryl U6070 (from Johnson Polymer)
0.05 g 0.1M potassium ferricyanide solution
0.05 g 0.1M potassium ferrocyanide solution
20 microL 50 mM potassium chloride solution Formulation IIId Oil:
0.475 g 2-3% aminopropylmethylsiloxane-dimethylsiloxane copolymer (Gelest, AMS132, 100 cSt)
0.475 g 10% acrylated siloxane (Rhodia, Rhodosil R01194, 800 cSt)
0.025 g α-hydroxycyclohexylphenylketone (Aldrich, 405612)
0.025 g αα-dimethyl-α-phenylacetophenone (Fluka, 38781)

Water:
0.02 g Triton ×100
0.125 g 0.1M potassium ferricyanide solution
0.125 g 0.1M potassium ferrocyanide solution
15 microL 50 mM potassium chloride solution Formulation IVa
1.0 g Fotecoat 1010 emulsion (FOTEC AG)
0.05 g 0.1M ferrocene
0.05 g 0.1M ferrocinium
20 microL 50 mM potassium chloride solution Formulation IVb Oil:
1.0 g 10% acrylated siloxane (Rhodia, Rhodosil R01194, 800 cSt)
0.025 g α-hydroxycyclohexylphenylketone (Aldrich, 405612)
0.025 g αα-dimethyl-α-phenylacetophenone (Fluka, 38781)

Water:
0.053 g polyvinylalcohol (Fluka, 18-88), derivatized with 2.75% (+/−0.25%) SBQ
1.3 g DI water
21 microL 50 mM potassium chloride solution Formulation IVc Oil:
1.0 g 10% acrylated siloxane (Rhodia, Rhodosil R01194, 800 cSt)
0.025 g α-hydroxycyclohexylphenylketone (Aldrich, 405612)
0.025 g αα-dimethyl-α-phenylacetophenone (Fluka, 38781)

Water:
0.052 g polyvinylalcohol (PolyScience 49-88)
1.3 g DI water
10 microL 50% glutaraldehyde aqeuous solution
0.052 g 0.1M potassium ferricyanide solution
0.052 g 0.1M potassium ferrocyanide solution
21 microL 50 mM potassium chloride solution In initial screening experiments at room temperature in a flow cell, all formulation families except those with SBQ derivatized polyvinylalcohol gave acceptable reference electrode performance (wet-up less than 100 seconds, minimal residual liquid junction potential). Formulations with SBQ derivatized polyvinylalcohol exhibited significant response to chloride, presumably being due to the ion exchange properties of the SBQ cation which is part of the hydrophilic compartment's cross-linking system. This data demonstrates that while the most straightforward method of reducing salt diffusion coefficient is by cross-linking of the hydrophilic matrix, the cross-linking chemistry may impart deleterious performance characteristics.

Although cross-linking of the hydrophilic compartment is a possible approach, we have found that cross-linking the hydrophobic compartment has been a more generally successful approach. Cross-linked acrylate derivatized siloxanes generally gave good results, with formulations containing less than 10% acrylate derivitization generally being superior. Highly acrylated siloxane formulations resulted in slower and more variable wet-up characteristics, particularly at 37° C.

In the above formulations, potassium chloride was often added to the hydrophilic compartment of membranes also loaded with potassium ferro and ferricyanide redox salts. It appears that the addition of potassium chloride does not significantly improve the performance of the membrane's salt bridge. We have found that the redox salts on their own, without additional other salts impart good salt bridge properties (either when using potassium ferrocyanide or potassium ferricyanide alone or in mixtures). This is presumably because the redox salts themselves are approximately equi-transferrent. We have found that the addition of potassium chloride at high concentration actually can degrade the performance. The hydrophilic compartment containing high potassium chloride content has variable drift characteristics and is shorter-lived because the additional salt causes the compartment to excessively swell during wet-up and become too permeable to salt transport. In contrast, ferro and/or ferricyanide salts added at high concentration may actually participate in cross-linking of the polyvinylalcohol binder, thus reducing salt diffusion coefficient and improving the use-life of the membrane. Even membranes prepared without any salt additions often give acceptable results. We infer from this that there are already some redox active contaminants in the membrane polymer systems (cross-linking agents, photoinitiators and the like) that can provide a low impedance interface with the gold electrode and poise its potential, and that salts in the calibrator fluid which permeate into the membrane during wet up provide the salt-bridge electrolyte. Generally however the gold electrodes are better poised when there is additional redox salt added to the membrane (less variable electrode voltage during wet up), and salt-bridge potentials are lower when the hydrophilic compartment has an approximately equi-transferent salt composition.

Our preferred formulation was of type IIIa. The resulting heterogeneous membrane comprised a hydrophobic compartment which was cross-linked 5% or 10% acrylated siloxane and the hydrophilic compartment comprised polyvinylalcohol binder. The hydrophilic compartment can contain one or both of potassium ferrocyanide and potassium ferricyanide with no additional salts. We have also prepared good membranes with very stable potentials after wet up when the redox compound was the mixed ferri-ferrocyanide, Prussian blue.

Oil and water components are gently mixed into a white 7-8 ml vial of about 15 mm diameter. The mixture is emulsified in the homogenizer at increasing speeds, as described earlier. This formulation resulted in membranes with a hydrophilic compartment (PVA) that is 5% by weight of the heterogeneous membrane. From gravimetric analysis we have estimated that after immersion of the membrane into an aqueous solution there is a few percent by weight water uptake into the membrane's hydrophilic compartment. For equilibrium water uptake of less than 10% by weight of the dry hydrophilic compartment, the salt loading in the dry membrane corresponds with a concentration of about 1M or larger of potassium ferro and ferricyanide. Salts are thus loaded to be present at or in slight excess of their saturation solubility in the wetted-up membrane.

Membranes cast from the preferred emulsion formulation were in the thickness range of 0.005 to 0.01 cm. Membranes cast on a gold electrode of an electrode module exhibited low noise and low resistance, wet up in under 60 seconds, minimal residual liquid junction response to compositional changes of the test solution and no redox interferences. When used as a reference electrode in combination with potentiometric indicator electrodes in a multi-sensor module in a diagnostic card operated at 37° C. we have obtained performance in conformance to clinically acceptable standards of precision and accuracy in measurements on whole blood.

Those skilled in the art of reference electrodes will recognize that there are many possible salt compositions that can be formulated to give a hydrophilic compartment containing approximately equi-transferrent electrolyte yielding a salt bridge with a minimum residual liquid junction potential. Such other formulations are possible so long as the hydrophilic compartment also contains redox species that react at the underlying metal electrode which poise its potential, and so long as the salt additions are compatible with a hydrophilic compartment having sufficiently low salt diffusion coefficient that the salt bridge has useful lifetime. Those skilled in the art of gas permeable membranes will recognize that there are many possible other materials for the hydrophobic compartment, so long as those materials can be formed into a membrane with an intimately admixed interpenetrating hydrophilic compartment, and so long as those materials permit rapid water vapor permeation.

Those skilled in the art will appreciate that the heterogeneous membrane of the invention can also be used with conventional reference electrode elements. For example a salt bridge using the invented heterogeneous membrane can be fabricated on a conventional silver-silver chloride electrode.

Prior Art Potentiometric Dissolved Carbon Dioxide Sensors

Figure 2A:
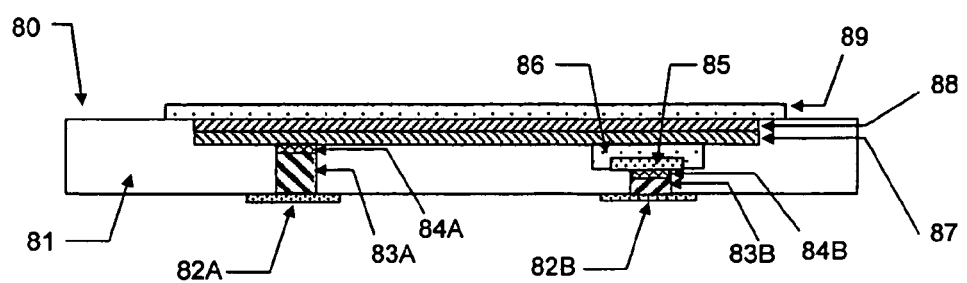
FIG. 2A is a cross-section through a prior-art planar potentiometric dissolved carbon dioxide electrode.

FIG. 2A shows a cross-section through a representative prior-art planar potentiometric dissolved carbon dioxide sensor similar to one described in the '184 patent. The device 80 which is part of a solid state electrode element in a disposable fluidic cartridge comprises a planar insulating substrate 81, with conductor elements 82A and 82B on one surface contacting two silver rod elements 83A and 83B with silver chloride over-layers 84A and 84B. One silver-silver chloride electrode 83A/84A is the internal reference electrode the other 83B/84B becomes the pH indicator electrode when coated with a thin film internal electrolyte element 85 and a pH sensitive membrane 86. Two additional hydrophilic matrix layers 87 and 88 containing chloride and bicarbonate salts together constitute the integral internal electrolyte overlaying the electrode pair. An outer gas permeable membrane 89 completes the sensor.

In use, the planar carbon dioxide sensor of the prior art is immersed in the solution to be tested so that the solution contacts the outer membrane 89 of the sensor. In this device, typical of the classical Severinghaus type dissolved carbon dioxide sensor of the prior art, the carbon dioxide is measured by the pH change within the hydrophilic elements 87 and 88. Carbon dioxide permeates through 89 and dissolves into layers 87/88 and is hydrolyzed to carbonic acid, which in turn ionizes to bicarbonate ions and protons. As is known in the art, the pH change in the internal electrolyte 87/88 measured by the voltage between the contacts to the indicator electrode 82B and internal reference electrode 82A is proportional to the logarithm of the carbon dioxide concentration change in the test solution when the bicarbonate and chloride concentrations in the internal electrolyte are constant. Non-volatile species are excluded from the internal electrolyte electrode region by element 89.

Potentiometric Dissolved Carbon Dioxide Sensors with Heterogeneous Membrane

Figure 2B:
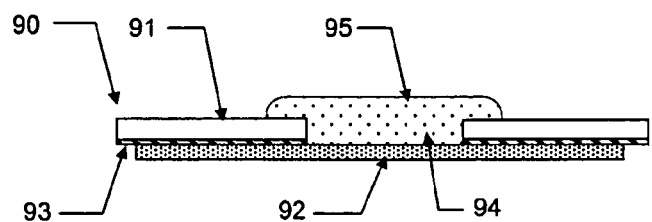
FIG. 2B is a horizontal cross-section of an embodiment of a potentiometric dissolved carbon dioxide electrode according to this invention.

FIG. 2B shows a horizontal cross-section of a preferred embodiment of the present invention directed to potentiometric dissolved gas electrodes, particularly to dissolved carbon dioxide electrodes. The invented device of FIG. 2B is remarkably simple when compared to the complex multi-layer device representative of the prior art. In the invented device there is only one electrode as opposed to the electrode pair of the conventional Severinghaus type device. The electrode is a metal only (no metal salt as in the standard silver-silver chloride technology). The electrode metal is the same as the metal material of the electric contact. The various hydrophilic membranes and gas permeable membranes used in prior-art devices are all now contained within either a single heterogeneous membrane coating of the metal electrode (singly coated embodiment) or in a double coating comprising in addition to the heterogeneous membrane a hydrophilic internal reservoir layer interposed between the heterogeneous membrane and the metal electrode (doubly coated embodiment). The electrode module 90 shown in cross-section includes an insulating foil 91 laminated with a metal foil element 92 and optional intermediate adhesive 93. A die-cut hole 94 through the insulator foil 91 determines the location of the electrode. The membranes 95 include at least a heterogeneous membrane comprising an intimate admixture of a hydrophobic polymeric compartment that is water vapor and carbon dioxide permeable (but not permeable to electrolyte) and a hydrophilic, electrolyte permeable compartment.

In the singly coated embodiment, the heterogeneous membrane's hydrophilic compartment constitutes the internal reagent reservoir which contains at least a bicarbonate salt and a pH sensitive redox couple that undergoes pH dependent reversible oxidation-reduction at the metal electrode. In a specific preferred embodiment of the single membrane device the electrode is gold, the heterogeneous membrane consists of polydimethylsiloxane hydrophobic polymer intimately admixed with a hydrophilic compartment that comprises a cross-linked polyvinylalcohol containing bicarbonate salt and quinhydrone. Other optional components are carbonic anhydrase, other electrolyte salts and surfactants.

In the doubly coated embodiment the internal reservoir layer interposed between the heterogeneous membrane and the electrode now contains at least bicarbonate salt and a pH sensitive redox couple, and optionally also carbonic anhydrase. In a preferred embodiment of the doubly coated electrode the internal reservoir layer is polyvinyl alcohol containing bicarbonate salt, quinhydrone salt and optional carbonic anhydrase. The heterogeneous membrane comprises a hydrophobic compartment with photo cross-linked acrylated siloxane (preferably less than 5% acrylated) and a hydrophilic compartment with polyvinyl alcohol (preferably less than 5% by volume of the heterogeneous membrane).

In use of the carbon dioxide sensor in accordance with the invention, electrical contact is made to the lower contact metal surface of the module by an external measuring circuit, thus contacting the indicator carbon dioxide electrode and a salt bridge reference electrode (also on the module but not shown in the above diagram). The upper surface of the module is first immersed in calibrator solution so that the solution is in contact with the outer heterogeneous membrane 95 of the sensor then, after a time t, it is immersed in a test solution whose $PCO_2$ is to be determined. When immersed in the calibrator solution, the heterogeneous membrane and the internal reagent reservoir wet up by water absorption through the hydrophobic compartment of the heterogeneous membrane, then by equilibrium partitioning from the hydrophobic compartment to the hydrophilic compartment and the internal reservoir. Electrical continuity between the indicator electrode and the external salt-bridge reference electrode is provided by electrical conduction through the heterogeneous membrane's hydrophilic compartment. Carbon dioxide in the calibrator solution also permeates the membrane by diffusion through the hydrophobic compartment, then by equilibrium partitioning from the hydrophobic compartment into the hydrophilic compartment and the internal reservoir. Carbon dioxide dissolves in the water within the aqueous pores of the hydrophilic compartment or the internal reservoir layer containing bicarbonate salt and pH dependent redox couple, where it hydrolyses forming hydrogen ions in accordance with the equilibrium relation shown in the following equation

$$CO_2 + H_2O \rightarrow H_2CO_3 \overset{K_1}{\rightleftharpoons} H^+ + HCO_3^- \overset{K_2}{\rightleftharpoons} 2H^+ + CO_3^{2-} \quad \text{Equation 3}$$

where $K_1$ and $K_2$ are the first and second dissociation constants of carbonic acid. A first pH established at the membrane's inner surface during immersion in calibrator leads to a first measurable electrode voltage, which voltage is related to the known $PCO_2$ in the calibrator solution. At time t the calibrator solution is removed and a test solution is brought in contact with the membrane. At this time a second electrode voltage corresponding to a second pH in turn related to the unknown $PCO_2$ in the test solution is measured. The measured milivolt response resulting from the pH change at the membrane's inner surface is related only to the $PCO_2$ concentration change between the calibrator and test solutions so long as the bicarbonate concentration at the membrane's inner surface is approximately constant through the period of time that the milivolt electrode responses are measured.

The hydrophobic gas permeable compartment of the heterogeneous membrane should be present in sufficient quantity to achieve sufficient and rapid (typically less than 60 seconds) water uptake into the initially substantially dry membrane during the calibration step, and to permit rapid equilibration of the heterogeneous membrane to the change in carbon dioxide concentration as the immersing solution is transitioned from calibrator to test solution.

During and after wet-up of the invented electrode there is continuous depletion of the heterogeneous membrane of those reagents initially incorporated into its hydrophilic compartment or its internal reservoir layer (bicarbonate salt and pH dependent redox electrolytes) by out-diffusion into the calibrator fluid. The concentration of these reagents in the heterogeneous membrane decreases through this time. The initial quantities of reagents in the membrane, the membrane's thickness and the reagents' diffusivity within the membrane's hydrophilic compartment determine the rate of change of reagent concentrations and the time to deplete the reagents to a critical threshold concentration level and the time to introduce contaminants to a critical concentration level, contaminants being buffers or redox contaminants that might interfere with the measurement. At the time t at which the test solution is applied to the electrode the reagent concentrations within the membrane should be at or above the required threshold concentration, and contaminants below a required threshold level at which the electrode's $PCO_2$ response slope is known and reproducible. Notably, the bicarbonate concentration should be in excess of the concentration of pH buffering moieties (but not larger than about 800 mM, at which concentration there is also appreciable carbonate and the electrode's response slope is depressed). In other words, the optimally performing device will exhibit a reproducible response slope to a change in the dissolved carbon dioxide concentration between the calibrator and the test solution up to a time t at which the bicarbonate concentration is in excess of buffer contaminants, and the pH dependent redox reagent is at a sufficient concentration excess over redox contaminants to constitute the potential determining electrode reaction.

The optimally performing device should also exhibit a speed of response to the change in the carbon dioxide concentration going from calibrator to test solution (which is the sensor signal) that is fast compared to the slower speed of response due to changes of other membrane reagent concentrations (the potential determining pH dependent redox electrolyte or the pH determining bicarbonate salts) as they diffuse out from the heterogeneous membrane and fast compared to the slower response due to contaminants (buffers or redox active species) diffusing into the membrane. Both the slow influx of contaminants and slow efflux of membrane reagents constitute an electrode drift during the time of transition between calibrator and test solutions. So long as the signal's time response is fast compared to these electrode drift responses the signal can be accurately extracted from the drift. To assure these conditions, it is preferred that the membrane's diffusion coefficient of carbon dioxide be much larger than the diffusion coefficient of the electrolyte salts initially loaded into the membrane. A heterogeneous membrane formulated with a low salt diffusion coefficient also impedes the transport of redox contaminants, protons or buffers from the test solution to the electrode surface where they might compete as the potential determining electrode reactants or where they might alter the internal pH and interfere with the pH determined by the hydrolysis of dissolved carbon dioxide.

Dissolved Carbon Dioxide Electrode Examples

To further understand the design rules for formulating the heterogeneous membrane of the dissolved carbon dioxide sensor according to this invention we present a number of exemplar membrane formulations and their sensor performance The preferred embodiments of the carbon dioxide electrodes in accordance with the invention are fabricated with a heterogeneous membrane coating step on top of a metal electrode which has a first coating of an internal reservoir layer. This reservoir layer comprises a hydrophilic matrix with the reservoir salts, bicarbonate and pH dependent redox salt and also containing carbonic anhydrase. It is also feasible to make carbon dioxide electrodes with only a single heterogeneous membrane coating the metal electrode. This requires the heterogeneous membrane's hydrophilic compartment to act as the internal salt reservoir containing bicarbonate and pH dependent redox reagent. In either case the heterogeneous membrane's gas permeable compartment permits water vapor transport to allow rapid wet-up of the internal reservoir, whether it be incorporated in a separate internal reservoir layer or as part of the heterogeneous membrane's hydrophilic compartment. The heterogeneous membrane's gas permeable path also permits rapid transport of carbon dioxide from the test solution to the internal reservoir where the carbon dioxide dissolves and changes the internal reservoir's pH. The hydrophilic compartment of the heterogeneous membrane permits transport of salts between the internal reservoir and the test solution to establish a liquid junction and provide electrical continuity to enable a potentiometric measurement versus an external reference electrode.

The preferred carbon dioxide electrodes comprised an inner reservoir layer formulated either with a chemically cross-linked polyvinylalcohol binder, or one that is not chemically cross-linked, as shown in the exemplar formulations recited below Cross-Linked Internal Reservoir:

0.07 g polyvinylalcohol (Fluka, 18-88), derivatized with 2.75% (+/−0.25%) SBQ
1.63 g DI water
0.1 g 0.1M benzoquinone (Sigma) solution
0.1 g 0.1M hydroquinone (Sigma) solution
0.22 g 0.2M sodium bicarbonate (Sigma) solution Addition of sodium bicarbonate is performed with vortexing Non Cross-Linked Internal Reservoir:

0.1 g polyvinylalcohol (PolyScience, 56-98)
1.15 g DI water
0.8 g 0.1M benzoquinone (Sigma) solution
0.11 g 0.1M hydroquinone (Sigma) solution
0.05 g 1M sodium bicarbonate (Sigma) solution
9 microL of 4% by weight carbonic anhydrase (Sigma) solution The benzoquinone to hydroquinone ratio need not be 1:1 as in the classical quinhydrone redox couple. The amount of hydroquinone loading is less critical than benzoquinone, indeed it can be completely absent. Generally higher concentrations of benzoquinone are preferred. Formulations were also made using other quinone based pH sensitive redox molecules of the known art such as thymoquinone in place of benzoquinone, giving similar results.

The heterogeneous membrane coating over the internal reservoir can be either cross-linked in the hydrophilic compartment using SBQ derivitized polyvinylalcohol, or it can be formulated with a cross-linked hydrophobic compartment as recited in the formulations below, cross-linking being photo initiated.

Polydimethylsiloxane/PVA-SBQ Heterogeneous Membrane Layer:

Oil:

1.5 g polydimethylsiloxane (Aldrich, 378402, 10,000 cSt)
0.5 g hexamethyldisiloxane (Aldrich, 205389)

Water:

0.06 g polyvinylalcohol (Fluka, 18-88), derivatized with 2.75% (+/−0.25%) SBQ
1.22 g DI water
0.2 g 0.2M potassium chloride solution
0.21 g 0.2M sodium bicarbonate solution Acrylated Siloxane/Polyvinylalcohol Heterogeneous Membrane Layer:

Oil:

2.0 g 5% acrylated siloxane (Gelest, USC-052, 150-200 cSt)
0.05 g ☐-hydroxycyclohexylphenylketone (Aldrich, 405612)
0.05 g ☐☐-dimethyl-☐-phenylacetophenone (Photo initiator, Fluka, 38781)

Water:

0.075 g polyvinylalcohol (Poly Science 49-88)
1.5 g DI water

The most preferred formulation for the heterogeneous membrane has used photo cross-linked acrylated siloxane formulations, the degree of acrylation being less than 5%.

We have used the quinhydrone couple (hydroquinone plus benzoquinone) as the pH dependent redox salt, but other pH dependent redox salts are known in the art and could also be used. (see for examples. J. Slattery et al. Coordination Chemistry Reviews 174, (1998) 391-416).

Experimental wet-up transients agree well with our computations (discussed below and shown in FIG. 3A). There is an initial wet up period (typically about 60 seconds or less) during which the electrode voltage increases rapidly as the dry bicarbonate in the internal reservoir acquires water and its pH decreases. A plateau is then achieved at which time the voltage increases more slowly as bicarbonate slowly diffuses out of the reservoir and its pH decreases slowly. We have targeted a dry bicarbonate salt loading which achieves an internal reservoir concentration in the range of 100 mM to 200 mM after membrane wet up. We can confirm that the target concentration has been achieved in the experimental membrane electrodes by observing their measured electrode potential after wet up, and knowing the pH dependence of the quinhydrone electrode we can compute the pH of the internal reservoir, and thus the bicarbonate concentration.

In the preferred embodiment of a singly coated carbon dioxide electrode using only a single heterogeneous membrane coating on the electrode there is no additional internal reservoir layer, and the bicarbonate salt, pH dependent redox salts and carbonic anhydrase are loaded into the hydrophilic compartment of the heterogeneous membrane which now constitutes the internal reservoir.

To better understand the desirable transport properties of the membrane of the electrode in accordance with the invention, we have generated design parameters based on simulations of the device's performance. Using a numerical finite element analysis of diffusion we computed the time and position transient species concentrations within the electrode's heterogeneous membrane. We computed the transient concentration of water, carbon dioxide, bicarbonate and the concentration of contaminating buffers at the membrane's inner surface contacting metal electrode versus time for different membrane salt diffusion coefficients, initial bicarbonate salt loading in the membrane and the membrane thickness. In these computations we simulated typical membrane formulations and dimensions that were investigated experimentally, comprising a polydimethylsiloxane hydrophobic compartment and a polyvinylalcohol hydrophilic compartment containing salts. We simulated membrane thicknesses in the range 80+/−20 micrometers. We modeled a heterogeneous membrane comprising 95%-98% by volume of a polydimethylsiloxane hydrophobic compartment with a tortuosity of 2 giving a membrane gas diffusion coefficient of $5 \times 10^{-6}$ for both water vapor and carbon dioxide, with solubility of $1 \times 10^{-3}$ and $6 \times 10^{-5}$ moles/cm$^3$/atm. for water vapor and carbon dioxide respectively. We assumed a hydrophilic compartment whose equilibrium water uptake was in the range 0.01 to 0.2 (total liquid water volume per membrane volume after wet-up being in the range $0.01 \times 2\%$ to $0.2 \times 5\% = 0.02\%$ to 1%). We assumed that carbon dioxide dissolved in the pore water of the hydrophilic compartment with a solubility of $2.3 \times 10^{-5}$ moles cm$^{-3}$atm.$^{-1}$ We considered an initially dry heterogeneous membrane electrode immersed in an aqueous solution. We computed the transient concentrations of water as the membrane wets up, of carbon dioxide, and of various salts: bicarbonate and pH dependent redox salts initially loaded into the membrane as they diffused out of the membrane into calibrator solution, and the concentration of contaminants (buffers, acids, bases and redox active species) as they diffused in. Our simulation computed these transient concentrations during the time period of initial wet-up in the calibrator liquid and the time when the calibrator is removed and a test solution is introduced to the electrode.

From this analysis we obtained species concentrations in the hydrophilic compartment at the inner membrane surface versus time. From these computed concentrations we could determine the electrode's carbon dioxide response slope. At the membrane's inner surface at time t the dissolved carbon dioxide at concentration $C_{dCO2}$ is in equilibrium with the bicarbonate and carbonate salts at concentrations of $C_{HCO3-}$ and $C_{CO3-}$. The proton concentration $C_{H+}$ (and pH given by pH=−LOG$_{10}C_{H+}$) of the hydrophilic compartment of the heterogeneous membrane at the inner boundary changes with dissolved carbon dioxide concentration and bicarbonate salt and buffer salt concentrations, which change can be computed from the following equilibrium equations:

the equation of mass balance for carbon containing species $$C_{NaHCO3} = C_{HCO3-} + C_{dCO2} + C_{CO3-} \quad \text{Equation 4}$$

the equation of mass balance for buffer species $$C_{HB} + C_{NaB} = C_{TB} \quad \text{Equation 5}$$

the charge balance equation $$C_{NaHCO3} + C_{NaB} = C_{B-} + C_{HCO3-} + 2C_{CO3-} \quad \text{Equation 6}$$

the 1st dissociation of carbonic acid $$C_{HCO3-} = K_1(C_{dCO2}/C_{H+}) \quad \text{Equation 7}$$

the 2nd dissociation of carbonic acid $$C_{CO3-} = K_2(C_{HCO3-}/C_{H+}) = K_1K_2(C_{dCO2}/C_{H+}^2) \quad \text{Equation 8}$$

the buffer equilibrium equation $$C_{B-} = C_{TB}/(1+(C_{H+}/K_B)) \quad \text{Equation 9}$$

The electrode potential is the sum of the potential difference between the electrode and the electrolyte in the hydrophilic compartment at the inner boundary due to the potential determining pH dependent redox reaction at the electrode surface plus the liquid junction potential between the membrane and the test solution. The potential at the electrode surface is determined by the pH in accordance with the equilibrium equation of the pH dependent redox couple. Using quinhydrone as example $$2H^+ + Q + 2e^- \leftrightarrow H_2Q \quad \text{Equation 10}$$

where the oxidant is benzoquinone (Q) and the reductant is hydroquinone (H$_2$Q), the electrode potential is given by $$V = V_{QH} + \frac{kT}{2q} Ln \frac{C_Q C_{H+}^2}{C_{H_2Q}} =$$
$$V_{QH} + \frac{kT}{2q} Ln \frac{C_Q}{C_{H_2Q}} + \frac{kT}{q} LnC_{H+} = Const - 0.06 \text{ pH}$$

Equation 11 where $C_Q$ and $C_{H2Q}$ are the concentrations of the benzoquinone and hydroquinone.

Figure 3:
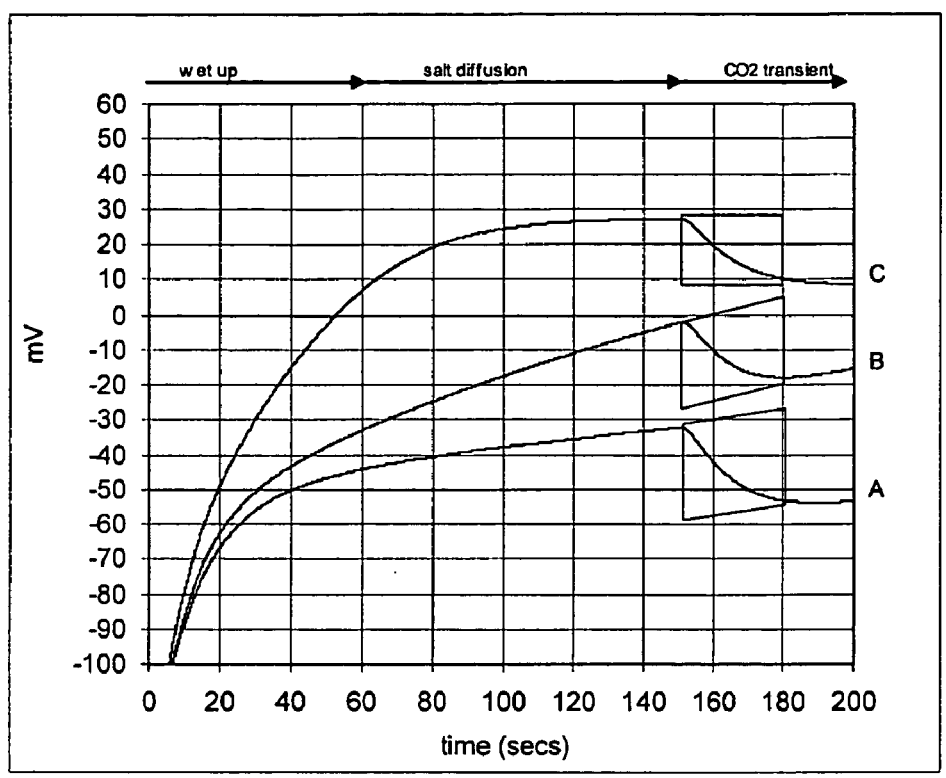
FIG. 3 is a graph of simulation data of carbon dioxide electrodes with heterogeneous membranes: electrode voltage versus time of three membranes having hydrophilic compartments with different salt diffusion coefficients A: $1\times10^{-7}$ $cm^2s^{-1}$, B; $3\times10^{-7}$ $cm^2s^{-1}$, C: $1\times10^{-6}$ $cm^2s^{-1}$.

We have computed the hydrogen ion concentration and thence the electrode milivolt response from the above quasi-equilibrium equations for different concentrations of carbon dioxide, bicarbonate and buffer salts in the membrane at the electrode surface at a time t after the commencement of the measurement, these concentrations being determined from the finite element analysis of diffusion. FIG. 3 shows a series of exemplar simulated voltage transients of electrodes of the invention. In this simulation we computed the response of three membranes, each loaded initially to a concentration of 400 mM sodium bicarbonate (calculated as the number of moles of dry bicarbonate salt initially loaded into the membrane divided by the volume of pore water at equilibrium wet-up). In the simulation, the membrane was initially immersed in a calibrator solution containing pCO$_2$ at 30 mm Hg, 30 mM bicarbonate and 50 mM of buffer comprising equal concentration of the buffer acid and the buffer's sodium salt and a pK of 7.4. At time t=150 seconds the membrane was immersed in a test solution containing PCO$_2$ at 10 mm Hg, bicarbonate at 30 mM and total buffer at 15 mM. We computed the voltage transients for three different salt diffusion coefficients: curve A at $1\times10^{-7}$, curve B at $3\times10^{-7}$ and curve C at $1\times10^{-6}$ cm$^2$/sec. The transients show an initial period of about 60 seconds of wet-up. At 60 to 150 seconds there is a monotonic voltage drift associated with slow bicarbonate efflux and buffer influx. The drift rate is larger for larger salt diffusion coefficients. At 150 seconds, when there is a switch from the calibrator to a test solution with a different PCO$_2$, the electrode responds to the PCO$_2$ change. The magnitude of the response is determined by the salt composition of the membrane's hydrophilic compartment at the inner surface at that point in time. As shown in the simulation, the membrane with a large salt diffusion coefficient (curve C) has been substantially depleted of bicarbonate and substantially contaminated with buffer so that the carbon dioxide response slope is diminished. We have repeated this computation for many membrane formulations with different bicarbonate loading and salt diffusion coefficients to further illustrate how the carbon dioxide response slope is affected by these parameters.

Figure 4:
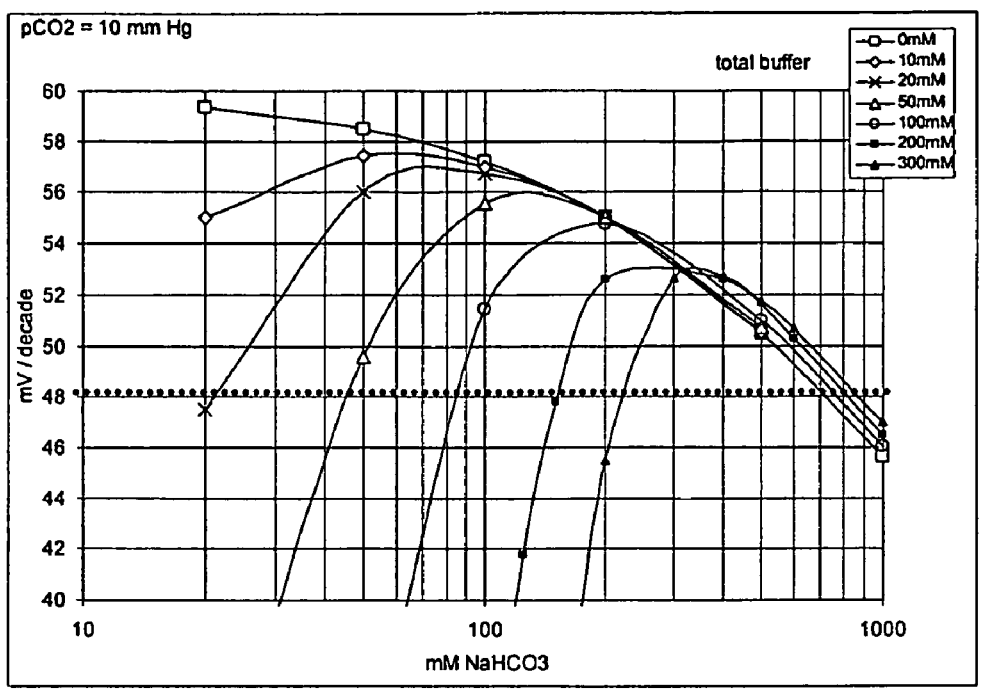
FIG. 4 is a graph of simulation data of carbon dioxide electrodes with heterogeneous membranes: electrode slope for different bicarbonate salt loading of the internal reservoir.

The graph of FIG. 4 shows the carbon dioxide response slope (milivolts output per decade change of PCO$_2$, for a transition form 30 mm Hg in the calibrator to 10 mm Hg in the test solution) versus bicarbonate and buffer concentration at the membrane's inner surface at time t when the switch from calibrator to test solution is made. This graph teaches that, as the bicarbonate content of the membrane is increased, the pH at the membrane's inner surface becomes more basic, the concentration of carbonate increases and the response slope is reduced. Thus there is an upper threshold for the preferred bicarbonate concentration that gives the best response slope. Using a cut-off of 48 mV/decade (0.8 of Nernst slope) as the minimally acceptable slope (corresponding to an acceptable range of 52+/−2 mV/decade we can specify the required bicarbonate concentration at time t. This preferred concentration of bicarbonate of the fully wet-up membrane at the inner boundary should be less than about 800 mM at the time t of measurement of the test solution. This graph also teaches that at low bicarbonate concentration in the membrane, the response slope is diminished as the concentration of contaminating buffer is increased. The amount of buffer is determined by the sum of that which has permeated into the membrane from the calibrator solution and any buffer contaminant incorporated initially into the membrane. Typically, a hydrophilic membrane binder such as polyvinylalcohol will contain proton binding sites which constitute internal buffers that are part of the membrane's hydrophilic compartment. Compositions of membranes with large internal buffer concentrations should be avoided to obtain good electrode response slope over a wide range of bicarbonate loading. The preferred minimum bicarbonate concentration for good electrode response is about 50 mM in the presence of buffer salts at a concentration of up to about 50 mM. A bicarbonate concentration of about 100 mM at the electrode surface at the time of measurement gives a CO$_2$ response slope in the range 52 to 56 mV per decade. Membranes with larger internal buffer concentrations can be tolerated, but the bicarbonate salt loading must be increased so that the bicarbonate concentration is in excess of buffers at the time of measurement.

TABLE 3

| | D cm$^2$/sec | | | | | | | | | |
|---|---|---|---|---|---|---|---|---|---|---|
| | $1\times10^{-7}$ | | | $2\times10^{-7}$ | | | $5\times10^{-7}$ | | | |
| | thickness cm | | | | | | | | | |
| | 0.01 | 0.008 | 0.006 | 0.01 | 0.008 | 0.006 | 0.01 | 0.008 | 0.006 | [HCO$_3^-$] |
| 100 secs | <0.8 | <0.8 | 0.85 | 0.80 | 0.84 | 0.91 | 0.88 | 0.93 | 0.83 | 800 mM |
| 200 secs | 0.82 | 0.85 | 0.91 | 0.87 | 0.92 | 0.91 | 0.93 | <0.8 | <0.8 | |
| 300 secs | 0.85 | 0.89 | 0.94 | 0.92 | 0.93 | <0.8 | <0.8 | <0.8 | <0.8 | |
| 100 secs | 0.85 | 0.88 | 0.90 | 0.87 | 0.91 | 0.94 | 0.93 | 0.94 | <0.8 | 400 mM |
| 200 secs | 0.89 | 0.91 | 0.94 | 0.92 | 0.94 | <0.8 | 0.89 | <0.8 | <0.8 | |
| 300 secs | 0.91 | 0.93 | 0.92 | 0.94 | 0.90 | <0.8 | <0.8 | <0.8 | <0.8 | |
| 100 secs | 0.91 | 0.93 | 0.95 | 0.93 | 0.95 | 0.94 | 0.94 | 0.90 | <0.8 | 200 mM |
| 200 secs | 0.93 | 0.94 | 0.93 | 0.95 | 0.93 | <0.8 | 0.83 | <0.8 | <0.8 | |
| 300 secs | 0.94 | 0.94 | 0.88 | 0.93 | 0.87 | <0.8 | <0.8 | <0.8 | <0.8 | |

In conclusion the preferred bicarbonate loading of the membrane is between 50 mM and 800 mM at the time of measurement.

Figure 5:
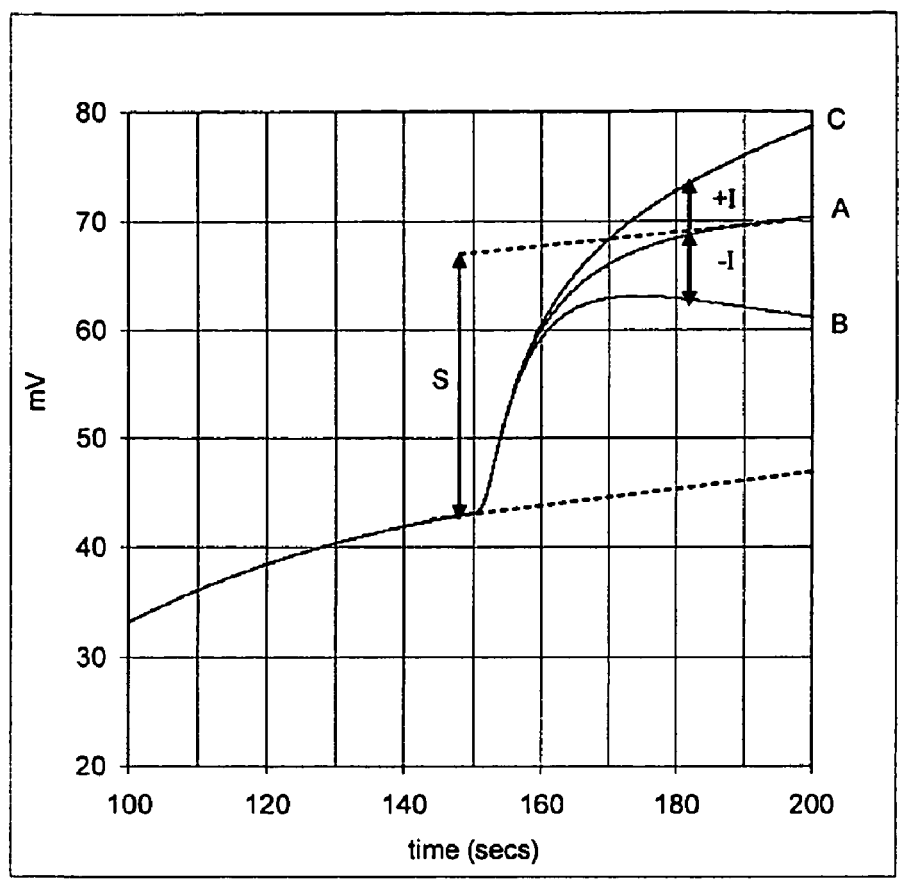
FIG. 5 is a graph of simulation data of carbon dioxide electrodes with heterogeneous membranes: bicarbonate interference data A: sample with normal bicarbonate B: sample with high bicarbonate C: sample with low bicarbonate concentration.

We have computed the transient response of heterogeneous membrane electrodes when there is a transition from calibrator to test fluid at a time t after the initial immersion of the electrode in calibrator. Typical computations are shown in FIG. 5. In this simulation, an initially dry heterogeneous membrane electrode is initially loaded with sodium bicarbonate and quinhydrone. The electrode is first immersed in a calibrator solution whose composition is PCO$_2$=30 mm Hg, concentration of bicarbonate at 30 mM and buffer (pK=7.5) concentration of 50 mM, then immersed in a test solution with PCO$_2$=100 mm Hg, at different bicarbonate concentrations spanning the clinical range from 10 to 60 mM, and 15 mM buffer. The transient response when switching between calibrator and test solutions at t=150 seconds at constant bicarbonate concentration is curve A showing a response time of about 30 seconds to PCO$_2$ superimposed on a monotonically drifting background. The background drift is associated with the continuous slow efflux of the bicarbonate initially loaded into the membrane from the fully wet-up membrane. The signal (S) is the milivolt response to the change in PCO$_2$ between calibrator and test solutions. The same device when exposed to a test solution with high bicarbonate concentration responds according to curve B, and low bicarbonate concentration curve C. The difference between these voltage transients at the point in time that the electrode has fully responded to the PCO$_2$ change is the bicarbonate interference I. The different voltage transients result because during the time after the fluid switch when carbon dioxide diffuses into the membrane to establish a new equilibrium pH at the inner membrane surface the bicarbonate in the test solution also diffuses into or out of the membrane and affects the membrane's internal pH. The degree to which there is bicarbonate interference is determined by the relative rate of diffusion of carbon dioxide gas and bicarbonate salt. This in turn depends on the relative diffusion rates of gas and salt and the total initial bicarbonate loading.

To further illustrate this we have computed the bicarbonate interference for a range of membranes with different initial salt loading, salt diffusion coefficient. We have computed the bicarbonate interference (I) in units of % change of $PCO_2$ per 10 mM change in bicarbonate concentration. The membrane thickness was 0.008 cm. These simulated data are shown in the table below.

TABLE 4

| Secs | $1 \times 10^{-7}$ | $2.5 \times 10^{-7}$ | $5 \times 10^{-7}$ | |
|---|---|---|---|---|
| 100 | 0.01 | 0.5 | 4.7 | 800 mM |
| 200 | 0.02 | 1.4 | 10.3 | |
| 300 | 0.03 | 2.5 | 11.1 | |
| 100 | 0.03 | 1.0 | 7.5 | 400 mM |
| 200 | 0.04 | 2.1 | 10.9 | |
| 300 | 0.06 | 2.9 | 11.2 | |
| 100 | 0.06 | 1.7 | 10.1 | 200 mM |
| 200 | 0.08 | 2.8 | 11.2 | |
| 300 | 0.11 | 3.3 | 11.2 | |

The conclusions from the above simulation data are:
 For a membrane with a carbon dioxide gas diffusion coefficient of $5 \times 10^6$ cm$^2$/sec the marginally acceptable salt diffusion coefficient is $5 \times 10^{-7}$ cm$^2$/sec, and then only when the initial bicarbonate loading in the membrane is high (<800 mM) and the measurement time is short (t<100 secs). This corresponds with a minimum diffusion constant ratio, $D_{gas}/D_{salt}$ of about 10. A faster responding carbon dioxide response is tolerant to a faster bicarbonate response, but the minimally acceptable ratio of diffusion coefficient remains the same.
 Preferred membranes have a diffusion coefficient ratio of 20 at which ratio there is lower bicarbonate interference, and still more preferred is 50 or larger, at which ratio there is no resolvable bicarbonate interference.

Prior Art Polarographic Oxygen Sensors

Figure 6A:
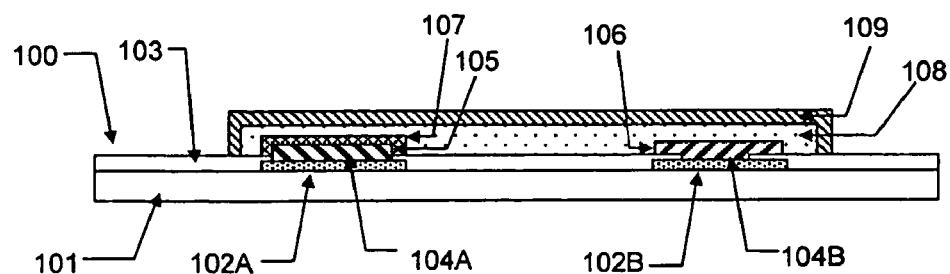
FIG. 6A is a cross-section through a prior-art planar polarographic oxygen sensor.

FIG. 6A illustrates a representative planar polarographic Clarke type oxygen sensor of the prior art. The device 100 shown in cross-section consists of a planar insulating substrate 101 supporting a metal layer 102 formed into two conducting elements 102A and 102B, and an insulating layer 103 overlaying them. Openings 104A and 104B through the insulating layer define the position of two electrodes, an indicator electrode and an internal reference electrode. Elsewhere on conductors 102A and 102B a contact is made to an external measuring circuit. Conductor element 102A is coated by films of silver and silver chloride formed into elements 105 and 107 constituting the internal silver/silver chloride reference-counter electrode. Conductor element 102B is coated by a film of gold formed into an electrode element 106 which is the indicator electrode. A film of a hydrophilic electrolyte medium 108 covers both electrodes. Electrolyte film 108 provides electrical continuity between electrodes at 104A and 104B. A film of a gas permeable, electrolyte impermeable material is formed into a cover element 109 that coats electrolyte film 108.

In use, the illustrative planar device of the prior art is immersed in the solution to be tested so that the solution contacts the outer membrane 109 of the sensor. Oxygen dissolved in the test solution is transported through gas permeable element 109 into the internal electrolyte reservoir 108 to the polarographic indicator electrode at 104B. Non-volatile electro-active species are excluded from the electrode region by layer 109. In this device, typical of the classical polarographic dissolved oxygen electrode of the prior art, the oxygen concentration is analyzed by measuring the oxygen reduction at the gold electrode. Typically, a cathodic voltage of several hundred milivolts is applied to the gold electrode versus the internal reference electrode. Electrical continuity between internal reference electrode and the cathode is through the internal reservoir layer 108 which is electrically isolated from the test solution by layer 109. As is known in the art, the current flowing between the two electrodes is proportional to the diffusion current of oxygen to the reducing electrode, which in turn is proportional to the oxygen concentration in the test solution.

Polarographic Oxygen Sensors with Heterogeneous Membrane

Figure 6B:
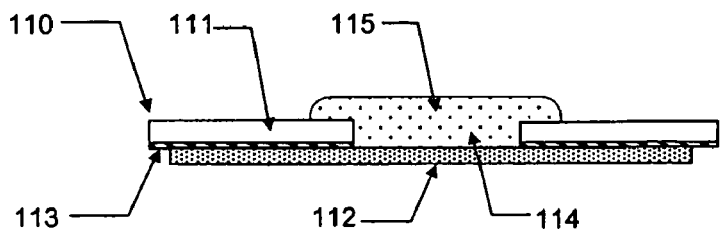
FIG. 6B is a cross-section through an embodiment of a planar polarographic oxygen sensor according to this invention.

The invented device of FIG. 6B is remarkably simple when compared to the complex multi-layer device representative of the prior art. In the invented device there is only one electrode. The electrode is a metal only (no metal salt as in the standard silver-silver chloride technology). The metal is the same as the metal contact material. The various hydrophilic membranes and gas permeable membranes used in prior-art devices are all now contained within a single heterogeneous membrane. The electrode module 110 shown in cross-section includes an insulating foil 111 laminated with a conducting metal foil element 112 and optional intermediate adhesive 113. A die-cut hole 114 through the insulator foil 111 determines the location of the electrode. The heterogeneous membrane 115 consists of a hydrophobic polymeric compartment that is water vapor and oxygen permeable (but not permeable to electrolyte) and a hydrophilic, electrolyte permeable compartment. In a preferred embodiment of this device the electrode is gold, the heterogeneous membrane consists of a cross-linked hydroxyl derivatized epoxy hydrophobic polymer admixed with a hydrophilic compartment that comprises cross-linked polyvinylalcohol. Additional optional components of the hydrophilic compartment of the membrane are surfactants, buffers and electrolyte salts.

In use of the invented polarographic oxygen sensor, electrical contact to an external measuring circuit is made to the lower contact metal surface of the module. The upper surface is immersed in calibrator solution so that the solution is in contact with the outer heterogeneous membrane 115 of the sensor. The heterogeneous membrane wets up by water absorption through the hydrophobic compartment of the membrane, then by equilibrium partitioning from the hydrophobic compartment to the hydrophilic compartment. Oxygen in the calibrator solution also permeates the membrane by diffusion through the hydrophobic compartment, then by equilibrium partitioning from the hydrophobic compartment into the hydrophilic compartment including the hydrophilic compartment at the surface of the metal electrode, which constitutes the sensor's internal reservoir. A cathodic voltage of several hundred millivolts is applied to the electrode versus an external reference-counter electrode (not shown). Electrical continuity between the sensor's electrode at 112 and the solution containing the external reference/counter electrode is by electrical conduction through the hydrophilic compartment of the heterogeneous membrane 115. Electrolyte transport through the hydrophilic compartment of the heterogeneous membrane 115 also permits out-diffusion of salts and other non-volatile reagents from the surface of electrode element 112 and in-diffusion of contaminants and interferents from the test solution, but their rate of diffusion being sufficiently slow that they do not reach a concentration sufficient to cause erroneous oxygen measurement during the time of the use of the device. This behavior is in marked contrast to prior-art devices. The oxygen dissolved in the hydrophilic compartment at the membrane's inner surface is reduced at the cathodic electrode. The reduction current is proportional to the oxygen concentration at the inner surface which is also proportional to the known concentration in the calibrator solution. At a time t the calibrator solution is removed and a test solution is brought into contact with the sensor's membrane. The oxygen concentration in the hydrophilic compartment at the membrane's inner surface changes to a new value proportional to the concentration of oxygen in the test solution, the cathodic electrode current now being proportional to the concentration of oxygen in the test solution.

In a preferred formulation of the heterogeneous membrane in accordance with the invention, the hydrophilic compartment of the heterogeneous membrane is confined to a small fraction of the total membrane volume, typically about 5% by volume or less, and the permeability of the hydrophilic compartment to redox active chemicals in the test solution is sufficiently small so that the electrode current due to interfering redox reactions is small compared to the signal current due to reduction of the dissolved oxygen being analyzed. The lower limit for the volume fraction of the hydrophilic compartment of the heterogeneous membrane is determined by the requirement for electrical continuity across the membrane element. Under normal measurement circumstances the heterogeneous membrane's bulk resistance should be less than about $10^8$ ohm to assure electrical continuity, not to incur a significant voltage drop through the membrane's thickness, and to have immunity from noise.

The oxygen permeability of a preferred heterogeneous membrane composition should be sufficiently low so that oxygen conductance through the membrane is lower than through the fluid above the membrane. With this condition there is minimal concentration polarization in the fluid and the electrode's oxygen response is not dependent on the fluids's flow rate or its hydrodynamic mixing. Also, a heterogeneous membrane whose hydrophobic compartment comprises a material with high oxygen permeability will likely also have large oxygen solubility. Such membranes are slower to respond and are therefore not favored. To estimate the upper limit of the desirable oxygen permeability of the membrane we first calculate oxygen conductance through the aqueous fluid above the membrane. For a macro-electrode, this is given approximately by the planar diffusional flux per unit area per unit pressure. The conductance is given by $C=P/x$, where P is the permeability of oxygen in the fluid through a diffusion layer of thickness x, x being in the range 0.005 cm (flowing fluid)$\leq x \leq 0.05$ cm (stagnant fluid). The oxygen permeability P through an aqueous fluid is the diffusion coefficient ($2\times10^{-5}$ cm$^2$s$^{-1}$) times the solubility ($1.5\times10^{-6}$ mole cm$^{-3}$atm$^{-1}$) which is $P=3\times10^{-11}$ mole cm$^{-1}$s$^{-1}$atm$^{-1}$. This gives a conductance in the range $6\times10^{-10} \leq C \leq 6\times10^{-9}$ mole cm$^{-2}$s$^{-1}$atm$^{-1}$. To avoid concentration polarization of the aqueous fluid above the membrane electrode, the conductance through the membrane, $C_m$, should be much smaller (say no more than 20%) of the conductance through the aqueous fluid. This sets an upper limit on the membrane's conductance and thence also its oxygen permeability $P_m$ for a given membrane thickness d, given by $C_m=P_m/d \leq 0.2\times6\times10^{-10}=1.2\times10^{-10}$ mole cm$^{-2}$s$^{-1}$atm$^{-1}$. For a membrane whose thickness is $5\times10^{-3}$ cm, which is typical, the preferred maximum oxygen permeability is then about $6\times10^{-13}$ mole cm$^{-1}$s$^{-1}$atm$^{-1}$. This result teaches that heterogeneous membranes with hydrophobic compartments comprising less oxygen permeable materials are more suitable than those using siloxanes whose permeability exceeds the desired upper limit (see Table I). Our formulation data described below confirm this finding. A heterogeneous membrane with a hydrophobic compartment having high oxygen permeability can still be useful, but only when the membrane's oxygen permeability can be reduced by a highly cross-linked hydrophilic compartment, so that the oxygen conductance through the highly cross-linked hydrophilic compartment at the electrode surface becomes the rate determining transport step. In the alternative a highly cross-linked additional internal reservoir layer can be interposed between the electrode and the heterogeneous membrane. However, membranes with too high permeability of their hydrophobic compartment, having also high oxygen solubility, are still not preferred because they are slower to respond. In a preferred membrane whose oxygen conductance is $C_m \leq 1.2\times10^{-10}$ mole cm$^{-2}$s$^{-1}$atm$^{-1}$ immersed in an air-saturated calibrator fluid at 0.2 atmospheres oxygen, the oxygen flux to the electrode is $2.4\times10^{-11}$ mole cm$^{-2}$s$^{-1}$ which corresponds with an electrode current density of about $1\times10^{-5}$ amps cm$^{-2}$ (assuming 4 electron cathodic reduction of oxygen).

Examples of Membranes for Oxygen Electrodes

To better understand the design rules for construction of polarographic oxygen electrodes according to this invention we present a number of exemplar heterogeneous membrane formulations and their sensor performance. Table 5 includes membrane formulations in which the hydrophobic compartment comprises a polymer system derived from a number of different families. These include siloxanes, acrylate derivatized siloxanes, hydroxyl derivatized epoxies, polyvinylacetate and urethanes. Examples of membranes are given comprising of cross-linked hydrophobic polymers, cross-linked hydrophilic polymers and both hydrophobic and hydrophilic polymers being cross-linked.

TABLE 5

| Hydrophobic compartment | Hydrophilic compartment | Oxygen membrane formulation # |
|---|---|---|
| Non-crosslinked | Non-crosslinked | I |
| Non-crosslinked polydimethylsiloxane | Crosslinked SBQ derivatized polyvinylalcohol | II a |
| polydimethylsiloxane | polyvinylalcohol with ammonium dichromate | b |
| Crosslinked acrylated siloxane | Non-crosslinked Polyvinyl alcohol | III a |
| Crosslinked acrylated siloxane | Crosslinked polyvinylalcohol/ acrylate crosslinked | IV a |
| acrylated epoxy polyol | polyvinylalcohol/ diazo crosslinked | b |
| polyvinylacetate | polyvinylalcohol | c |

Formulation IIb

Oil:

1.32 g polydimethylsiloxane (Sigma-Aldrich, 1,000 cSt)

Water:

0.71 g polyvinylalcohol solution (Fluka, 18-88-dissolved in DI water to 21% solids)

116 microL 1M ammonium dichromate solution 37.5 microL 2M potassium chloride solution 1.6 mL DI water 1. Dilute the polyvinylalcohol solution with DI water and salt solutions.
2. Emulsify oil and water at 24,000 rpm for about 1 minute.

3. Print membranes, allow to dry at room temperature for about 15 minutes, then expose for 30 seconds to low-power UV Formulation IIIa Oil:

1.48 g Zipcone-UA (100%-acrylated siloxane, Gelest)

Water:

1.71 mL DI water 0.105 g PEG(1000) diacrylate (1000 molecular weight polyethylene glycol terminated at both ends with acrylate, Polysciences—diluted to 48% in DIW and with 2.5% 2-hydroxy-4'-(2-hydroxyethoxy)-2-methylpropiophenone dissolved in it (photoinitiator, Sigma-Aldrich))

0.923 g polyvinylalcohol (18-88, Fluka—dissolved in DI water to 19% solids)

43 microL 2M potassium chloride solution

1. Dilute the pre-dissolved PVA and PEG(1000) diacrylate with the DI water, add potassium chloride solution, vortex.
2. Add the siloxane oil and emulsify at 6,000 to 8,000 rpm for about 2 minutes, then at 24,000 rpm for about 1 minute.
3. Print membranes, allow to dry at room temperature for 15 minutes, then expose to UV (5 exposures of 2 seconds each).

Formulation IVa

Oil:

1.475 g Zipcone-UA (100%-acrylated siloxane, Gelest)

Water:

2.24 mL DI water 0.07 g PEG(1000) diacrylate (1000 molecular weight polyethylene glycol terminated at both ends with acrylate, Polysciences—diluted to 48% in DI water and with 2.5% 2-hydroxy-4'-(2-hydroxyethoxy)-2-methylpropiophenone dissolved in it (photoinitiator, Sigma-Aldrich))

0.8 g polyvinylalcohol (18-88, Fluka—dissolved in DIW to 19% solids)

0.15 g Diazo-LZ (polyvinylalcohol crosslinker, Esprix—dissolved to 10% in DI water)

38 microL 2M potassium chloride solution

1. Dilute the pre-dissolved polyvinylalcohol and PEG (1000) diacrylate with the DI water, add potassium chloride solution, vortex.
2. Add the siloxane oil and homogenize at low speed for about 2 minutes, then at top speed for about 1 minute.
3. Print membranes, allow to dry at room temperature for 15 minutes, then expose to UV (5 exposures of 2 seconds each).

Formulation IVb

Oil:

1.625 g Ebecryl 6040 (Acrylated-Epoxy-Polyol, UCB)

0.195 g Irgacure-500 (Photoinitiator, Ciba)

0.048 g Irgacure-369 (Photoinitiator, Ciba)

0.0075 g Zonyl FSN (Surfactant, DuPont)

Water:

1.888 g DI water 1.079 g polyvinylalcohol (18-88, Fluka: dissolved in DI water to 14% solids)

0.15 g diacetone acrylamide (Reactive monomer, DSM Fine Chemicals)

0.0075 g Dapro DF-900 (Defoamer, Elementis Specialties)

0.012 g Diazo-DDAM-12 (polyvinylalcohol cross-linker, Materiali Sensibili—dissolved to 3.1% in DI water)

1. Dilute the pre-dissolved polyvinylalcohol with the DI water, then dissolve into it the diacetone acrylamide.
2. Add the rest of the ingredients and emulsify at 6,000 to 8,000 rpm for about 2 minutes, then at 24,000 rpm for about 1 minute.
3. Filter through 12 micrometer syringe filter.
4. Add Diazo cross-linker to filtered emulsion and mix.
5. Let sit for 1 hour to degas, then print membranes.
6. Let air-cure for 15 minutes then expose to UV for 4 seconds.

The epoxy polyols: Ebercyl 6040 and 608 also gave similar results. Other IVb type formulations that we tested included acrylated urethanes copolymerized with polyols, giving similar results to the epoxies. Formulations based on blends of the acrylated epoxy-polyols with acrylated urethane-polyols also gave similar results.

Formulation IVc 1.575 g Vinac 285 (Polyvinylacetate emulsion, Air Products)

0.82 mL DI water 0.56 g polyvinylalcohol (18-88, Fluka—dissolved in DIW to 19% solids)

0.332 g trimethylolpentane triacrylate (Sigma-Aldrich, with 1% benzoin ethyl ether (photoinitiator, Sigma-Aldrich) dissolved in it)

0.04 g dibutyl fumarate (plasticizer, Scientific Polymer Products)

30 microL 2M potassium chloride solution

1. Vortex until homogeneous.
2. Print membranes, allow to dry at room temperature for about 15 minutes, then expose to UV for 4 seconds.

Electrodes were fabricated by micro-dispensing oil in water emulsion membrane cocktails over the electrode orifice of an electrode module. For a typical device, the electrode orifice was a 0.08 cm diameter hole in an epoxy foil overlaying a gold foil electrode, having an electrode area of $5 \times 10^{-3}$ cm$^2$. Approximately 1 mm diameter membranes were cast with a dry thickness in the range 2 to $5 \times 10^{-3}$ cm. For an electrode of this geometry and a preferred current density of less than $1 \times 10^{-5}$ amps cm$^{-2}$ in air-saturated calibrator the preferred maximum calibrator current of the electrodes is $5 \times 10^{-8}$ amps.

Formulations in the IVb family were our preferred formulations. All preferred formulations meet the desired electrode performance criteria for use in dissolved oxygen measurements in clinical applications. When used as an oxygen electrode in a multi-sensor module in a diagnostic card operated at 37° C. we have obtained performance in conformance to clinically acceptable standards of precision and accuracy in measurements on whole blood.

Electrodes with preferred membrane formulations wet-up within 100 seconds when they are $3 \times 10^{-5}$ cm thickness or less. They have a current density less than the desirable upper limit of $1 \times 10^{-5}$ amps cm$^{-2}$ when they are thicker than $1.5 \times 10^{-3}$ cm. Response time (100% response) to oxygen is 30 seconds or less when the membrane is less than $3 \times 10^{-5}$ cm thickness. Therefore the preferred thickness range for the preferred membrane formulations is between about $1.5 \times 10^{-3}$ to $3 \times 10^{-3}$ cm.

Those skilled in the art will recognize that many other biosensor electrodes such as enzyme electrodes can be made with very simple membrane construction when using the inventive principles.

What is claimed is:

1. An electrode for use in an electrochemical sensing device for the analysis of an aqueous sample, comprising;
   an insulating substrate layer having first and second sides, the insulating substrate layer having an opening defining an electrode region;
   an electric conductor located on the first side of the insulating substrate layer and closing the aperture on the first side; and
   a dry heterogeneous membrane for direct contact with the sample, the heterogeneous membrane being located on the second side of the insulating substrate layer and closing the aperture on the second side, the heterogeneous membrane being in electric contact with the conductor in the electrode region, the heterogeneous membrane including a hydrophobic compartment, a hydrophilic compartment and a dry internal reagent reservoir, the hydrophobic compartment being gas permeable and having a water vapor diffusion coefficient, the hydrophilic compartment being electrolyte salt permeable and having an aqueous electrolyte diffusion coefficient, wherein the hydrophobic compartment is in excess of the hydrophilic compartment for the water vapor diffusion coefficient of the hydrophobic compartment to be higher than the aqueous electrolyte diffusion coefficient of the ion conducting electrolyte compartment to maintain the electrode in a substantially dry, inactive condition at ambient conditions and to render the electrode convertible into a wet-up, active condition by water vapor penetration through the hydrophobic compartment into the internal reagent reservoir upon exposure of the heterogeneous membrane to an aqueous liquid.

2. The electrode as defined in claim 1, wherein the hydrophilic compartment incorporates the internal reagent reservoir.

3. The electrode as defined in claim 1, further comprising a dry hydrophilic layer in electrical contact with the conductor in the electrode region, wherein the heterogeneous membrane is in physical contact with the insulating substrate layer at the electrode region and in electrical contact with the hydrophilic layer in the electrode region, at least one of the hydrophilic layer and the hydrophilic compartment of the heterogeneous membrane incorporating the internal reservoir.

4. The electrode as defined in claim 3, wherein the internal reservoir includes reagents and the membrane in the active condition, upon exposure to the aqueous sample fluid, permits diffusion of the reagents from the internal reservoir into the sample fluid.

5. The electrode as defined in claim 4, wherein the heterogeneous membrane in the active condition further permits diffusion of contaminants into the membrane layer.

6. The electrode as defined in claim 1 for use in a unit-use disposable salt-bridge reference electrode.

7. The electrode as defined in claim 1 for use in a unit-use disposable potentiometric gas sensor.

8. The electrode as defined in claim 1 for use as a unit-use disposable polarographic gas electrode.

9. The electrode as defined in claim 1, wherein the conductor is a gold layer.

10. The electrode as defined in claim 1, wherein the heterogeneous membrane is a layer cast from a liquid.

11. The electrode as defined in one of claim 1, wherein the heterogeneous membrane is cast from an oil in water emulsion.

12. The electrode as defined in claim 11, wherein the oil portion of the emulsion comprises a polymer or polymer precursor, or a mixture of polymers or polymer precursors, or derivatized polymers or polymer precursors selected from the following polymer families: polysiloxanes, polyurethanes, polyphosphazenes, polybutadienes, polyisoprenes, epoxies and polyvinylacetates.

13. The electrode as defined in claim 11, wherein the water portion of the emulsion comprises a dissolved polymer or a polymer precursor, or a mixture of polymers or derivatized polymers selected from the following group of polymer families: polyvinylalcohols, polyhydroxymethacrylates, polyacrylamides, polysaccharides, cellulosic polymers and gelatins.

14. The electrode as defined in claim 10, wherein the heterogeneous membrane is cast by a method selected from the group of printing by dispensing through a nozzle, pin-transfer printing, spin-coating, dip-coating, and screen-printing.

15. The electrode as defined in claim 1, wherein the hydrophobic compartment comprises a polymer or a derivatized polymer, or a mixture of polymers or derivatized polymers selected from the following group of polymer families: polysiloxanes, polyurethanes, polyphosphazenes, polybutadienes, polyisoprenes, epoxies, polyvinylacetates and combinations thereof.

16. The electrode as defined in claim 1, wherein the hydrophilic compartment includes a hydrophilic polymer or a mixture of polymers including derivatized polymers selected from the following group of polymer families: polyvinylalcohols, polyhydroxyacrylates, polyacrylamides, polysaccharides, cellulosic polymers and gelatins and combinations thereof.

17. The electrode of claim 1, for use in a sensing device constructed for sequential exposure of the electrode to an aqueous calibrator fluid and the sample fluid.

18. The electrode of claim 1, wherein the hydrophobic compartment includes a gas permeable polymer and the hydrophilic compartment includes a hydrophilic polymer, at least one of the hydrophobic polymer and the hydrophilic polymer being cross-linkable.

19. The electrode of claim 18, wherein the at least one polymer is at least partially cross-linked.

20. The electrode of claim 19, wherein the at least one polymer was cross-linked by a photo-initiated cross-linking process.

21. The electrode of claim 18, wherein the membrane is cast from a liquid and the cross-linking is performed after casting.

22. The electrode of claim 1, wherein the water vapor diffusion coefficient is at least 10 times larger than the salt aqueous electrolyte diffusion coefficient.

23. The electrode of claim 22, wherein the water vapor diffusion coefficient is at least 50 times larger than the aqueous electrolyte diffusion coefficient.

24. The electrode of claim 1, wherein the water vapor diffusion coefficient is greater than $1 \times 10^{-6}$ cm$^2$s$^{-1}$ and the aqueous electrolyte diffusion coefficient is less than $1 \times 10^{-7}$ cm$^2$s$^{-1}$.

25. The electrode of claim 1, wherein the hydrophilic compartment is less than 5% by volume of the total volume of the heterogeneous membrane.

26. The electrode of claim 1, wherein the electric conductor is a metal foil and the insulator is a foil laminated thereto.

27. The electrode as defined in claim 2 for use as a potentiometric reference electrode, wherein the internal reservoir also includes a redox salt for electrochemical reaction at the electric conductor.

28. The electrode as defined in claim 27 for use as a potentiometric reference electrode, wherein the hydrophilic compartment comprises a salt composition which is approximately equi-transferrent.

29. The electrode as defined in claim 27, wherein the redox salt is selected from the group of ferrocyanide, ferricyanide, Prussian blue and combinations thereof.

30. The electrode as defined in claim 1 for use as a potentiometric reference electrode, wherein the heterogeneous membrane comprises a hydrophobic compartment containing acrylated siloxane and a hydrophilic compartment containing polyvinylalcohol.

31. The electrode of claim 1 for use as a polarographic oxygen electrode, wherein the heterogeneous membrane has an oxygen permeability of less than $6 \times 10^{-13}$ mole $cm^{-1}s^{-1}atm^{-1}$.

32. The electrode of claim 1 for use as a polarographic oxygen electrode wherein the hydrophobic compartment contains a compound selected from the group of acrylated epoxy, acrylated urethane, blends thereof and copolymers of at least one of acrylated epoxy and acrylated urethane with a polyol, and the hydrophilic compartment contains polyvinylalcohol.

33. The electrode of claim 2 for use as a potentiometric carbon dioxide electrode, wherein the internal reservoir contains bicarbonate salt and a pH sensitive redox salt.

34. The electrode of claim 33, wherein the internal reservoir also contains carbonic anhydrase.

35. The electrode of claim 33, wherein the pH sensitive redox salt is selected from the group of hydroquinone, benzoquinone, and combinations thereof.

36. The electrode of claim 33, wherein the membrane layer is in a substantially dry, inactive condition and convertible into a wet-up, active condition by exposure to an aqueous fluid and the bicarbonate salt is loaded into the dry internal reservoir in an amount to give a concentration in the range of 50 mM to 800 mM after wet up.

37. The electrode of claim 1 for use as a potentiometric carbon dioxide electrode, wherein the hydrophobic compartment contains acrylated siloxane and the hydrophilic compartment contains polyvinylalcohol.

38. The electrode of claim 2 for use in an electrochemical sensing apparatus for the analysis of an enzyme substrate in an aqueous sample, wherein the internal reservoir contains an enzyme and a redox salt.

* * * * *

UNITED STATES PATENT AND TRADEMARK OFFICE
CERTIFICATE OF CORRECTION

| | |
|---|---|
| PATENT NO. | : 7,767,068 B2 |
| APPLICATION NO. | : 10/856929 |
| DATED | : August 3, 2010 |
| INVENTOR(S) | : Imants Lauks et al. |

Page 1 of 1

It is certified that error appears in the above-identified patent and that said Letters Patent is hereby corrected as shown below:

Column 42, claim 22, line 57, delete "salt".

Signed and Sealed this

Ninth Day of November, 2010

David J. Kappos
*Director of the United States Patent and Trademark Office*